United States Patent [19]

Anderson et al.

[11] 4,374,838

[45] Feb. 22, 1983

[54] DIBENZO[a,d]CYCLOOCTEN-5,12-(AND 6,12)-IMINES

[75] Inventors: Paul S. Anderson, Lansdale; Marcia E. Christy, Perkasie; Ben E. Evans, Lansdale; David C. Remy, North Wales, all of Pa.

[73] Assignee: Merck & Co., Inc., Rahway, N.J.

[21] Appl. No.: 313,900

[22] Filed: Oct. 22, 1981

Related U.S. Application Data

[60] Division of Ser. No. 80,896, Oct. 1, 1979, Pat. No. 4,329,465, which is a continuation-in-part of Ser. No. 917,044, Jun. 19, 1978, abandoned, which is a continuation-in-part of Ser. No. 834,343, Sep. 19, 1977, abandoned.

[51] Int. Cl.$^3$ ............................................ A61K 31/435
[52] U.S. Cl. .................................................... 424/256
[58] Field of Search ......................................... 424/256

*Primary Examiner*—Stanley J. Friedman
*Attorney, Agent, or Firm*—William H. Nicholson; Mario A. Monaco

[57] ABSTRACT

Dibenzo[a,d]cycloocten-5,12-(and 6,12)-imines, derivatives and pharmaceutically acceptable salts thereof are useful as anxiolytics, antidepressants, anticonvulsants, muscle relaxants and in the treatment of mixed anxiety-depression, minimal brain dysfunction and extrapyramidal disorders such as Parkinson's disease.

4 Claims, No Drawings

DIBENZO[a,d]CYCLOOCTEN-5,12-(AND 6,12)-IMINES

This is a division of application Ser. No. 80,896, filed Oct. 1, 1979, now U.S. Pat. No. 4,329,465, which is a continuation-in-part of copending application Ser. No. 917,044, filed June 19, 1978 (abandoned), which, in turn, is a continuation-in-part of application Ser. No. 834,343, filed Sept. 19, 1977 (abandoned).

BACKGROUND OF THE INVENTION

This invention is concerned with dibenzo [a,d]cycloocten-5,12-(and 6,12)-imines, derivatives, optical isomers and pharmaceutically acceptable salts thereof which are useful as anxiolytics, antidepressants, anticonvulsants, muscle relaxants and in the treatment of mixed anxiety-depression, minimal brain dysfunction and extrapyramidal disorders such as Parkinson's disease.

Structurally related compounds are known in the art to have qualitatively similar utilities. For example U.S. Pat. No. 3,892,756 discloses 10,11-dihydro-5H-dibenzo[a,d]cyclohepten-5,10-imine and derivatives and Belgian Pat. No. 829,075 discloses 9,10-dihydroanthracen-9,10-imines and derivatives.

It is an object of this invention to provide a new class of compounds known as dibenzo[a,d]cycloocten-5,12-(and 6,12)-imines; novel processes for their synthesis; pharmaceutical compositions comprising them as active ingredient; and a novel method of treatment where there is an indicated need for an antianxiety agent, muscle relaxant, or a treatment for extrapyramidal disorders.

It is a further object of this invention to provide key intermediates, 5,6-dichloro-5,12-dihydro-12-oxodibenzo[a,d]cyclooctene and 6-chloro-5,12-dihydro-12-oxodibenzo[a,d]cyclooctene.

DETAILED DESCRIPTION OF THE INVENTION

The novel compounds of this invention have structural formula:

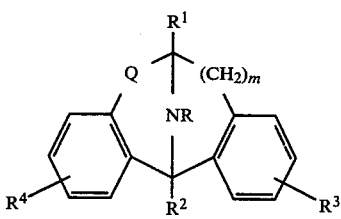

or a pharmaceutically acceptable salt thereof, wherein:
m is 0 or 1;
Q is —$CH_2$— when m is 1, or
Q is —$CH_2CH_2$— or —CH=CH— when m is 0;
R is
  (1) hydrogen,
  (2) lower alkyl, especially $C_{1-3}$ alkyl,
  (3) lower alkenyl, especially $C_{2-3}$ alkenyl,
  (4) phenyl-lower alkyl, especially phenyl-$C_{1-3}$ alkyl, preferably benzyl, and
  (5) lower cycloalkyl, especially $C_{3-6}$ cycloalkyl,
  (6) lower(cycloalkyl-alkyl), especially $C_{3-6}$ cycloalkyl-$C_{1-3}$alkyl, or
  (7) di(lower alkyl)amino-lower alkyl, especially dimethylaminopropyl;
$R^1$ is
  (1) hydrogen,
  (2) lower alkyl, especially $C_{1-3}$ alkyl,
  (3) lower alkenyl, especially $C_{2-3}$ alkenyl,
  (4) phenyl-lower alkyl, especially phenyl-$C_{1-3}$ alkyl, preferably benzyl, or
  (5) lower cycloalkyl, especially $C_{3-6}$ cycloalkyl;
$R^2$ is
  (1) hydrogen,
  (2) lower alkyl, especially $C_{1-3}$ alkyl,
  (3) lower alkenyl, especially $C_{2-3}$ alkenyl,
  (4) phenyl-lower alkyl, especially phenyl-$C_{1-3}$ alkyl, preferably benzyl, or
  (5) lower alkoxy, especially $C_{1-3}$ alkoxy; or
  (6) di(lower alkyl)amino-lower alkyl, especially dimethylaminopropyl; and
$R^3$ and $R^4$ are independently
  (1) hydrogen,
  (2) halogen, especially fluoro, chloro, or bromo, preferably bromo,
  (3) lower alkoxy, especially $C_{1-3}$ alkoxy,
  (4) trifluoromethylthio,
  (5) cyano,
  (6) carboxy, or
  (7) hydroxy.

A preferred embodiment of the novel compounds of this invention is that wherein R is hydrogen, lower alkyl, or benzyl, $R^1$ is hydrogen or lower alkyl, $R^2$ is hydrogen or lower alkyl, and $R^3$ and $R^4$ are hydrogen.

An even more preferred embodiment of the novel compounds is where R is hydrogen, lower alkyl or benzyl, and $R^2$ is lower alkyl, especially methyl or ethyl, and $R^1$, $R^3$ and $R^4$ are all hydrogen.

The novel compounds of this invention where m is 1 have structural formula:

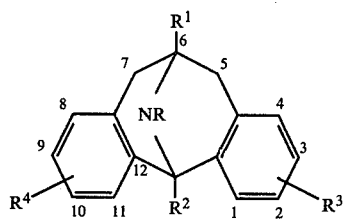

They are prepared by a variety of processes, depending to some extent on the type of substitution present in the final product.

Compounds with a 12-halo substituent, are useful intermediates in the preparation of compounds wherein $R^2$ is hydrogen, alkoxy or alkyl.

The 12-bromo- or chloro- compounds are converted to the 12-hydrogen compounds by hydrogenolysis with a metal hydride such as lithium aluminum hydride, or sodium borohydride, or by catalytic hydrogenation. The hydride reactions are conducted in an anhydrous medium in the absence of oxygen preferably in an ethereal solvent such as ether, tetrahydrofuran, dioxane or the like at a temperature between about −10° C. and 30° C.

Where $R^2$ is lower alkoxy, the compounds are readily prepared by treatment of the 12-bromo- or 12-chloro-compounds with the appropriate sodium or potassium lower alkoxide in the corresponding lower alkanol as solvent by refluxing for 4 to about 10 hours.

In those compounds wherein $R^2$ is lower alkyl, they can be prepared by treatment of the corresponding 12-bromo-or chloro- compound with the appropriate lower alkyl lithium. The reaction is conducted in an anhydrous solvent such as benzene, ether, or the like at a temperature of about $-10°$ C. to about $+10°$ C. for one to about four hours.

Many of the novel compounds particularly those wherein $R^2$ is lower alkyl, phenyl-lower alkyl or lower alkenyl are prepared by formation of the imine bridge. The reaction comprises treating a 6-substituted-amino-12-lower alkylene compound with a strong base such as potassium or sodium hydroxide in a hydroxylic solvent such as ethylene glycol at 150°–250° C. for 12–36 hours. The substituents on the 6-amino group may be any of those groups included in the definition of R and may also be acetyl. The ring closure also proceeds smoothly under the influence of an organometallic such as butyl lithium in an ethereal solvent such as tetrahydrofuran, 1,2-dimethoxyethane or the like at temperatures between about 0° C. and about 35° C., preferably at room temperature for about 30 minutes to about 5 hours.

Similarly a 6-hydroxylamino-12-alkylene compound undergoes cyclization to form a 12-alkyl-6,12-N-hydroxyimine. This in turn on treatment with nascent hydrogen, preferably from zinc in acetic acid without temperature control followed by 1-5 hours at 50°–80° C., is reduced to the N-unsubstituted 12-alkyl-6,12-imine compound.

These N-unsubstituted imines can then be substituted with an R group by treatment with an appropriate R-halide such as chloride, bromide or iodide in a solvent such as dioxane, tetrahydrofuran, or ether, in the presence of an acid acceptor such as an inorganic base such as sodium carbonate, an organic base such as pyridine or a basic resin at reflux temperature for 2–5 days.

The novel compounds of this invention where m is 0 and Q is —CH₂—CH₂ or —CH=CH— have structural formula:

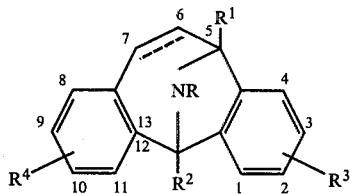

They are prepared by a variety of processes, depending to some extent on the type of substitution present in the final product.

Compounds with a 12-halo substituent, are useful intermediates in the preparation of compounds wherein $R^2$ is hydrogen, alkoxy or alkyl.

The 12-bromo- or chloro- or 6-chloro- compounds are converted to the respective 12- and 6- hydrogen compounds by hydrogenolysis with a metal hydride such as lithium aluminum hydride, or sodium borohydride, or by catalytic hydrogenation. The hydride reactions are conducted in an anhydrous medium in the absence of oxygen preferably in an ethereal solvent such as ether, tetrahydrofuran, dioxane or the like at a temperature between about $-10°$ C. and 30° C.

In the case of the 6-chloro—$\Delta^{6,7}$-5,12-imines, catalytic hydrogenation reduces the double bond and hydrogenolyzes the chloro group. On the other hand, the hydrides merely hydrogenolyze the chloro group.

In those compounds wherein $R^2$ is alkyl, they can be prepared by treatment of the corresponding 12-bromo- or chloro- compound with the appropriate alkyl lithium. The reaction is conducted in an anhydrous solvent such as benzene, ether, or the like at a temperature of about $-10°$ C. to about $+10°$ C. for one to about four hours.

Many of the novel compounds particularly those wherein $R^2$ is alkyl or substituted alkyl are prepared by formation of the imine bridge. One reaction comprises treating a 5-substituted-amino-12-alkylene compound with a strong base such as potassium or sodium hydroxide in a hydroxylic solvent such as ethylene glycol at 150°–250° C. for 12–36 hours. The substituents on the 5-amino group may be any of those groups included in the definition of R and may also be acetyl. The ring closure also proceeds smoothly under the influence of an organometallic such as butyl lithium in an ethereal solvent such as tetrahydrofuran, 1,2-dimethoxyethane or the like at temperatures between about 0° C. and about 35° C., preferably at room temperature for about 30 minutes to about 5 hours.

Novel compounds having substituents on the benzenoid rings are generally prepared by metathesis of the appropriate bromo compound. For example treatment with a sodium or potassium lower alkoxide in the presence of copper dust in a solvent such as dimethylformamide at 50°–150° C. for 1–10 hours produces the corresponding lower alkoxy compound.

These lower alkoxy compounds are converted to the hydroxy analogs by de-etherification, preferably by heating with pyridine hydrochloride at 200°–220° C. for 3–10 hours.

Similarly treatment of a bromo compound with cuprous cyanide in a solvent such as dimethylformamide at reflux temperatures for 1–10 hours yields the corresponding cyano compound.

Hydrolysis of the above cyano compounds with a mineral acid such as hydrochloric acid at reflux temperature produces the corresponding carboxy substituted compounds.

Also treatment of the bromo compounds with bis(trifluoromethylthio)mercury and copper dust in a solvent such as dimethylformamide at reflux temperature for 1–10 hours yields the trifluoromethylthio derivatives.

The starting materials and processes used for preparing the intermediates used in the above described processes are fully described in the Examples.

Also included within the scope of the present invention are the non-toxic pharmaceutically acceptable salts of the novel compounds. Acid addition salts of the imine compounds are formed by mixing a solution of the imine with a solution of a pharmaceutically acceptable non-toxic acid such as hydrochloric acid, fumaric acid, maleic acid, succinic acid, acetic acid, citric acid, tartaric acid, carbonic acid, phosphoric acid, or the like. Where the novel compound carries a carboxylic acid group, the invention also contemplates sodium, potassium, and calcium salts thereof.

The 5,12-imines of this invention, and the 6,12-imines having a substituent on a benzenoid ring are resolvable into optical isomers such as by formation of diastereomeric pairs with an optically active acid followed by fractional crystallization and regeneration of the optically active free bases.

Further embodiments of this invention are the novel key intermediates of structure

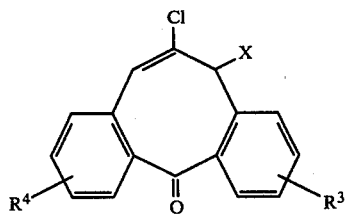

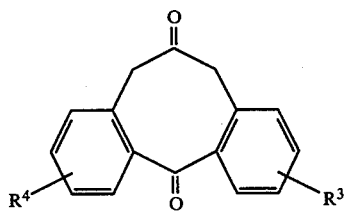

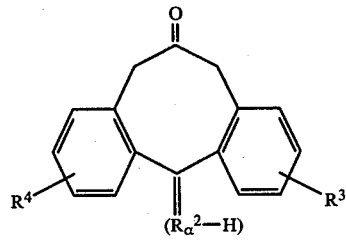

wherein X is hydrogen or chloro and $R^3$ and $R^4$ are independently hydrogen or halo such as bromo, chloro or fluoro, and $R_\alpha^2$ is lower alkyl, lower alkenyl, phenyl-lower alkyl or di(lower alkyl)amino-lower alkyl.

The processes for preparation of these key intermediates is as shown by the following reaction scheme, and are fully described in the Examples that follow:

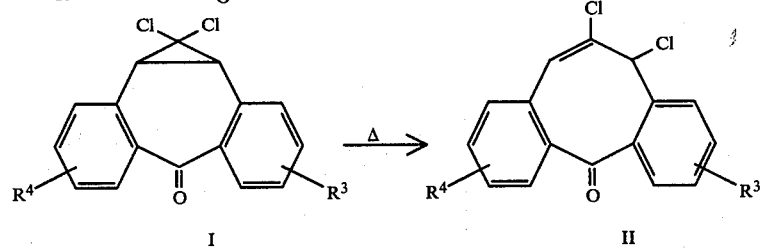

I            II

LiAlH$_4$

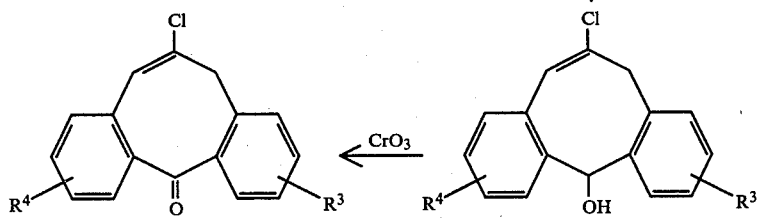

IV            III

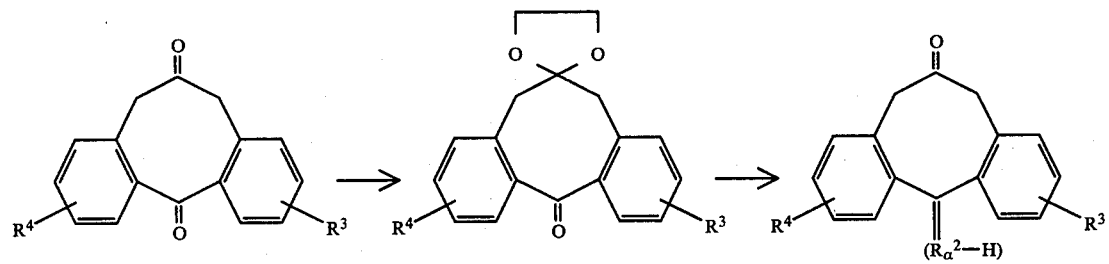

In the method of treatment aspect of the present invention, the novel dibenzocycloocten-6,12-imines of this invention are capable of producing anxiety relief without causing excessive sedation or sleep at a dosage level of from about 0.01 to about 50 mg. per kilogram of body weight preferably about 0.05–10 mg/kg. of body weight on a regimen of 1–4 times a day. In addition, the novel compounds of the present invention are useful as muscle relaxants, antidepressants, anticonvulsants and in the treatment of mixed anxiety-depression, minimal brain dysfunction and extrapyramidal disorders when indicated, at comparable dosage levels. It is understood that the exact treatment level will depend upon the case history of the animal or human individual being treated and in the last analysis the precise treatment level falling within the above guidelines is left to the discretion of the therapist.

Also included within the scope of the present invention are pharmaceutical compositions comprising the imines of this invention. Preferably these compositions are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, i.e., conventional tableting ingredients such as corn starch, lactose, sucrose, sorbitol, talc, stearic acid, magnesium stearate, dicalcium phosphate, gums, and other pharmaceutical diluents, e.g., water, to form a solid preformulation composition containing a homogeneous mixture of an imine of the present invention, or a non-toxic pharmaceutically acceptable salt, thereof. When referring to these preformulation compositions as homogeneous, it is meant that the active ingredient, is dispersed evenly throughout the composition so that the composition may be readily subdivided into equally effective unit dosage forms such as tablets, pills, capsules, and the like. This solid preformulation composition is then subdivided into unit dosage forms of the type described above containing from 0.1 to about 500 mg. of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like.

The liquid forms in which the novel composition of the present invention may be incorporated for administration orally or by injection include aqueous solutions, suitably flavored syrups, aqueous or oil suspensions, flavored emulsions with edible oils such as cottonseed oil, sesame oil, coconut oil, peanut oil and the like, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone, gelatin and the like.

The following Examples repesentatively illustrate, but do not limit, the product, process, method of treatment, or compositional aspects of the present invention.

EXAMPLE 1

12-Bromo-13-methyl-5,6,7,12-tetrahydrodibenzo[a,d]cycloocten-6,12-imine

Step A: Preparation of
8,8-Dichloro-2,3,5,6-Dibenzobicyclo[5.1.0]octan-4-one

Into a flame-dried, nitrogen-flushed 500 ml. round bottom flask, provided with dropping funnel, stirrer, and condenser with calcium chloride drying tube, was placed 5H-dibenzo[a,d]cyclohepten-5-one (20.52 g., 0.1 mole), sodium methoxide (50 g., 0.925 mole) and 150 ml. of dry benzene. The mixture was stirred and cooled in an ice bath. Ethyl trichloroacetate (165 g., 0.85 mole) was added dropwise over a 3 to 4 hour period while stirring vigorously. After the addition had been completed, the mixture was stirred an additional 5 hours at 0° C. and then overnight at room temperature. Water (150 ml.) was added to hydrolyze the mixture. The benzene phase and a benzene extract of the aqueous phase were combined and the solvent was removed under reduced pressure on the steam bath. Trituration of the deep brown residue induced rapid crystallization. The solid product was collected and washed with cold methanol. Recrystallization from methanol gave 17.65 g. (61%) of product, m.p. 132°–133° C.

Step B: Preparation of
5,6-Dichloro-5,12-dihydro-12-oxo-dibenzo[a,d]cyclooctene

A mixture of 37 g. of 8,8-dichloro-2,3,5,6-dibenzobicyclo[5.1.0]octan-4-one and 200 ml. of nitrobenzene was heated under reflux for 4 hours. The solvent was steam distilled, and the residue was crystallized twice from acetonitrile to give 28 g. of 5,6-dichloro-5,12-dihydro-12-oxo-dibenzo[a,d]cyclooctene, m.p. 123°–125° C.

Step C: Preparation of
6-Chloro-5,12-dihydro-12-oxo-dibenzo[a,d]cyclooctene

A solution of 14.4 g. of dichloro-ketone from Step B in 75 ml. of tetrahydrofuran and 125 ml. of ether was added dropwise over 1 hour with stirring to a slurry of 3.8 g. of lithium aluminum hydride in 400 ml. of ether. The resulting mixture was refluxed for 10 minutes. Excess lithium aluminum hydride was consumed by dropwise addition of 13 ml. of water with stirring. The mixture was filtered and the inorganic residue was washed with ether. The combined filtrates were dried ($MgSO_4$), filtered and evaporated to dryness to give 13.8 g. of an oil. The oil was dissolved in 500 ml. of acetone and treated with 40 ml. of 1.4 molar chromium trioxide in aqueous sulfuric acid (70 g. $CrO_3$ + 61 ml. $H_2SO_4$ diluted to 500 ml. with water) added dropwise with stirring at 5° C. over 40 minutes. After stirring one more hour at room temperature, isopropanol was added dropwise to discharge the orange color. The acetone was decanted and the residue (A) was washed with acetone. The combined acetone solutions were evaporated to dryness (B). The residue (A) was dissolved in 200 ml. of water and extracted with 300 ml. of ether. The ether extract was added to residue (B) and the solution was extracted with water. The water extract was back extracted with 2×200 ml. of ether. The combined ether solutions were washed with 200 ml. of water and the water was back extracted with 150 ml. of ether. The combined ether phases were dried ($MgSO_4$), filtered and evaporated to dryness to give 12.7 g. of crude product which after recrystallization from methanol gave 10.6 g. (83%) of 6-chloro-5,12-dihydro-12-oxo-dibenzo[a,d]cyclooctene, m.p. 109°–110° C.

Step D: Preparation of
6,12-dioxo-5,6,7,12-tetrahydrodibenzo[a,d]cyclooctene

A mixture of 40 g. of monochloro-ketone from Step C and 240 ml. of n-butylamine was stirred and refluxed for 23 hours under anhydrous conditions. The mixture was evaporated to dryness *in vacuo*. The residue was dissolved in 800 ml. of 0.5 N hydrochloric acid, filtered and the filtrate was heated 2 hour on a steam bath. After cooling, the precipitate was collected, washed with a little water and dried to give 35 g. of 6,12-dioxo-5,6,7,12-tetrahydrodibenzo[a,d]cyclooctene, m.p. 158°-160° C.

Employing the procedure substantially as described in Example 1, Steps A through D, but substituting for the 5H-dibenzo[a,d]cyclohepten-5-one used in Step A thereof an equimolecular amount of 3-bromo-5H-dibenzo-[a,d]cyclohepten-5-one, 3-chloro-5H-dibenzo[a,d]cyclohepten-5-one, or 3-fluoro-5H-dibenzo[a,d]cyclohepten-5-one, and o-chlorobromobenzene as solvent in Step B, there are produced, respectively, 2-bromo-6,12-dioxo-5,6,7,12-tetrahydrodibenzo[a,d]cyclooctene, m.p. 133°-138° C., 2-chloro-6,12-dioxo-5,6,7,12-tetrahydrodibenzo[a,d]cyclooctene, m.p. 148°-149° C., and 2-fluoro-6,12-dioxo-5,6,7,12-tetrahydrodibenzo[a,d]cyclooctene.

Step E: Preparation of 12-hydroxy-13-methyl-5,6,7,12-tetrahydrodibenzo[a,d]cycloocten-6,12-imine A mixture of 4.72 g. (0.02 mole) of diketone from Step D and a solution of 3.93 g. of methylamine in 270 g. of tetrahydrofuran was stirred under anhydrous conditions at room temperature for 5 hours. After cooling to 10° C. 3.6 g. (0.06 mole) of acetic acid and 3.77 g. (0.06 mole) of sodium cyanoborohydride were added and the mixture was stirred 30 hours at room temperature. The supernatant was decanted and the precipitate was washed with benzene and ether. The combined supernatants and washings were evaporated *in vacuo* and the residue was partitioned between benzene, and 200 ml. of 1 N aqueous hydrochloric acid. The aqueous layer was separated, made basic with aqueous sodium hydroxide solution and the product was collected by filtration and washed with H₂O. Recrystallization from benzene gave 3.9 g. of 12-hydroxy-13-methyl-5,6,7,12-tetrahydrodibenzo[a,d]cycloocten-6,12-imine, m.p. 237°-239° C.

Employing the procedure substantially as described in Example 1, Step E, but substituting for the methylamine and for the 6,12-dioxo-5,6,7,12-tetrahydrodibenzo[a,d]cyclooctene, comparable amounts of an amine of formula R-NH₂ and/or a 2-substituted analog of the dioxo compound there are produced the R³-12-hydroxy-13-R-5,6,7,12-tetrahydrodibenzo[a,d]cycloocten-6,12-imines described in Table I, in accordance with the following reaction:

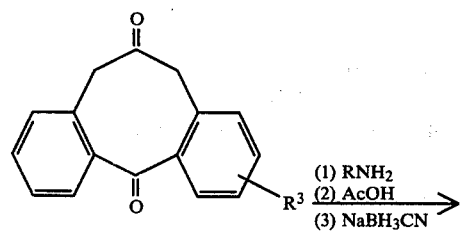

(1) RNH₂
(2) AcOH
(3) NaBH₃CN

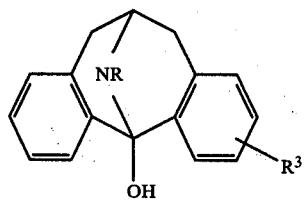

TABLE I

| R | R³ | R | R³ |
|---|---|---|---|
| —H | H | —H | 3-Br |
| —C₃H₇ | 2-Br | —CH₃ | 2-Br |
| —CH₂—CH=CH₂ | H | —CH₂—C₆H₅ | 2-Br |
| —CH₂—C₆H₅ | H | —CH₃ | 2-Cl |
| —cyclopropyl | H | —CH₂—C₆H₅ | 2-Cl |
| —cyclohexyl | 2-Br | —CH₃ | 2-F |
| —CH₂—cyclopropyl | H | —CH₂—C₆H₅ | 2-F |
| —CH₂CH₂—C₆H₅ | H | —(CH₂)₃N(CH₃)₂ | H |

Step F: Preparation of 12-bromo-13-methyl-5,6,7,12-tetrahydrodibenzo[a,d]cycloocten-6,12-imine A suspension of 2.5 g. of the carbinol from Step E, in 50 ml. of toluene was treated with 1.0 ml. of phosphorous tribromide and refluxed 6 hours. The mixture was concentrated to dryness and the residue was dissolved in a mixture of 250 ml. of water, 300 ml. of benzene:ether (1:1 v/v) and 25 ml. of 5% (w/v) aqueous sodium hydroxide at ice-bath temperature. The organic layer was separated and washed with cold water, dried (Na₂SO₄), filtered, and concentrated to dryness to give 2.7 g. of crude product, m.p. 135°-139° C. This material was chromatographed on 150 g. of silica gel by elution with chloroform saturated with ammonium hydroxide to give 2.0 g. of 12-bromo-13-methyl-5,6,7,12-tetrahydrodibenzo[a,d]cycloocten-6,12-imine, m.p. 142°-144° C., which after recrystallization from cyclohexane had m.p. 147°-149° C.

Employing the procedure substantially as described in Example 1, Step F, but substituting for the 12-hydroxy-13-methyl-5,6,7,12-tetrahydrodibenzo[a,d]cycloocten-6,12-imine used therein an equimolecular amount of the carbinols described in Table I, there are produced the respective 12-bromo compounds described in Table II in accordance with the following reaction.

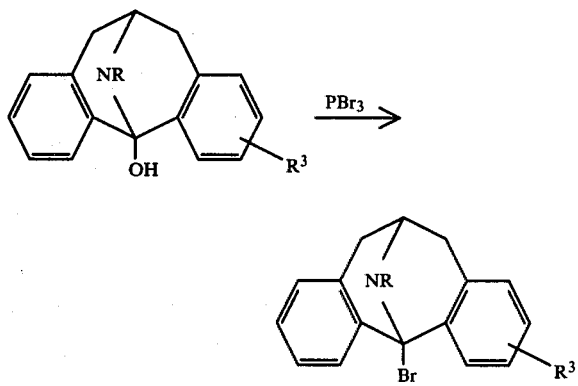

TABLE II

| R | R³ | R | R³ |
|---|---|---|---|
| —H | H | —H | 3-Br |
| —C₃H₇ | 2-Br | —CH₃ | 2-Br |
| —CH₂CH=CH₂ | H | —CH₂—C₆H₅ | 2-Br |
| —CH₂—C₆H₅ | H | —CH₃ | 2-Cl |
| —cyclopropyl | H | —CH₂—C₆H₅ | 2-Cl |
| —cyclohexyl | 2-Br | —CH₃ | 2-F |
| —CH₂—cyclopropyl | H | —CH₂—C₆H₅ | 2-F |
| —CH₂CH₂—C₆H₅ | H | —(CH₂)₃N(CH₃)₂ | H |

EXAMPLE 2

12-Ethyl-13-methyl-5,6,7,12-tetrahydrodibenzo[a,d]cycloocten-6,12-imine hydrochloride A solution of 3.1 g. of 12-bromo compound from Example 1, Step F in 270 ml. of absolute ether and 30 ml. of benzene was added dropwise over 70 minutes to 30 ml. of ethyl lithium in benzene (approximately 0.95 M) with stirring under nitrogen and external ice-bath cooling. After stirring in the cold for one more hour, excess ethyl lithium was destroyed by adding a few drops of water. The ether solution was washed with water until neutral, dried (Na₂SO₄), filtered, and concentrated to dryness. The residue was triturated with 50 ml. of hexane, decanted, and concentrated to dryness to give 1.95 g. of viscous yellow oil. The oil was chromatographed on 200 g. of silica gel by elution with a mixture of 10 volumes of 95% ethanol and 90 volumes of toluene, collecting 4 ml. fractions which were combined according to thin layer chromatographic comparisons. The third material to be eluted, fractions 43-70 comprised 650 mg. oily solid. This material (650 mg.) was dissolved in 5 ml. of warm methanol and treated with 0.3 ml. of 9 N HCl in ethanol. Dilution with 15 ml. of absolute ether caused crystallization of 550 mg. of a hydrochloride salt, m.p. 267°–269° C. (dec.) which on recrystallization from methanol-acetone gave 12-ethyl-13-methyl-5,6,7,12-tetrahydrodibenzo[a,d]cycloocten-6,12-imine hydrochloride, m.p. 273°–274° C.

Employing the procedure substantially as described in Example 2, but substituting for the 12-bromo-13-methyl-5,6,7,12-tetrahydrodibenzo[a,d]cycloocten-6,12-imine and/or the ethyl lithium used therein, equimolecular amounts respectively of the imines of Table II or Example 2 and an organometallic compound of formula $R_a^2$-Li, wherein $R_a^2$ is lower alkyl, lower alkenyl, phenyl-lower alkyl, or di(lower alkyl)amino-lower alkyl, there are produced the 13-R-12-$R_a^2$-R³-6,12-imines described in Table III in accordance with the following equation:

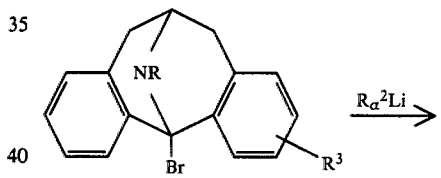

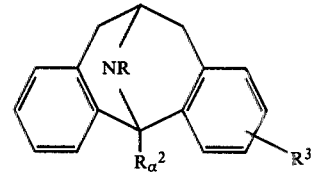

TABLE III

| R | $R_a^2$ | R³ | R | $R_a^2$ | R³ |
|---|---|---|---|---|---|
| H | —C₂H₅ | H | —CH₃ | —CH₂CH₂—C₆H₅ | H |
| —C₃H₇ | —C₂H₅ | 2-Br | —H | —C₂H₅ | 3-Br |
| —CH₂—CH=CH₂ | —C₂H₅ | H | —CH₃ | —C₂H₅ | 2-Br |
| —CH₂—C₆H₅ | —C₂H₅ | H | —CH₂—C₆H₅ | —C₂H₅ | 2-Br |
| —cyclopropyl | —C₂H₅ | H | —CH₃ | —(CH₂)₃N(CH₃)₂ | H |
| —cyclohexyl | —C₂H₅ | 2-Br | —CH₃ | —C₂H₅ | 2-Cl |

TABLE III-continued

| R | $R_a^2$ | $R^3$ | R | $R_a^2$ | $R^3$ |
|---|---------|-------|---|---------|-------|
| —CH$_2$—◁ | —C$_2$H$_5$ | H | —CH$_2$—Ph | —C$_2$H$_5$ | 2-Cl |
| —CH$_2$CH$_2$—Ph | —C$_2$H$_5$ | H | —CH$_3$ | —C$_2$H$_5$ | 2-F |
| —CH$_3$ | —CH$_2$CH=CH$_2$ | H | —CH$_2$—Ph | —C$_2$H$_5$ | 2-F |
| —CH$_3$ | —CH$_2$—Ph | H | —(CH$_2$)$_3$N(CH$_3$)$_2$ | —C$_2$H$_5$ | H |

EXAMPLE 3

12-Methoxy-13-methyl-5,6,7,12-tetrahydrodibenzo[a,d]cycloocten-6,12-imine

A mixture of 1.6 g. of 12-bromo-13-methyl-5,6,7,12-tetrahydrodibenzo[a,d]cycloocten-6,12-imine (Example 1), 0.3 g. of sodium methoxide and 30 ml. of methanol was refluxed 6 hours. The mixture was concentrated to dryness and the residue was stirred with 100 ml. of ether for 30 minutes. The mixture was filtered and the filtrate was concentrated to dryness to give 0.78 g. of 12-methoxy-13-methyl-5,6,7,12-tetrahydrodibenzo[a,d]cycloocten-6,12-imine, m.p. 70°–90° C., after which recrystallization from methanol-water had m.p. 91°–93° C.

Employing the procedure substantially as described in Example 3, but substituting for the 12-bromo-13-methyl-5,6,7,12-tetrahydrodibenzo[a,d]cycloocten-6,12-imine and the sodium methoxide used therein equimolecular amounts, respectively, of the 12-bromo-5,6,7,12-tetrahydrodibenzo[a,d]cycloocten-6,12-imines of Table II and sodium alkoxides defined in Table IV, there are produced the 12-alkoxy compounds also described in Table IV in accordance with the following equation:

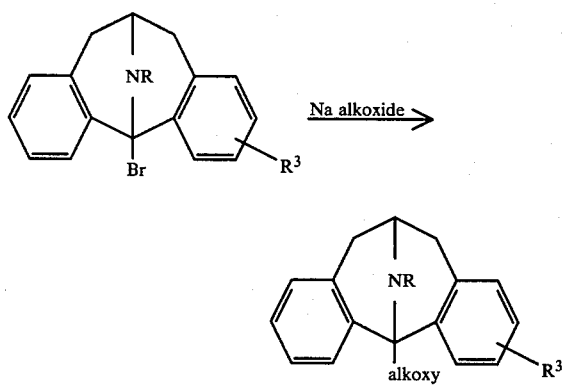

TABLE IV

| R | $R^3$ | alkoxy |
|---|-------|--------|
| H | H | —OCH$_3$ |
| —C$_3$H$_7$ | 2-Br | —OC$_2$H$_5$ |
| —CH$_2$CH=CH$_2$ | H | —OCH$_3$ |
| —CH$_2$—Ph | H | —OCH$_3$ |
| —◁ | H | —OC$_3$H$_7$ |
| —cyclohexyl | 2-Br | —OC$_2$H$_5$ |
| —CH$_2$—Ph | 2-Cl | —OCH$_3$ |
| —CH$_2$—Ph | 2-F | —OCH$_3$ |
| —CH$_2$—◁ | H | —OCH$_3$ |
| —CH$_2$CH$_2$—Ph | H | —OCH$_3$ |
| H | 3-Br | —OCH$_3$ |
| —CH$_3$ | 2-Br | —OCH$_3$ |
| —CH$_2$—Ph | 2-Br | —OCH$_3$ |
| —CH$_3$ | 2-Cl | —OCH$_3$ |
| —CH$_3$ | 2-F | —OCH$_3$ |

EXAMPLE 4

13-Methyl-5,6,7,12-tetrahydrodibenzo[a,d]cycloocten-6,12-imine oxalate

Step A: Preparation of 12-chloro-13-methyl-5,6,7,12-tetrahydrodibenzo[a,d]cycloocten-6,12-imine A mixture of 0.7 g. of 12-hydroxy compound from Example 1, Step E in 10 ml. of thionylchloride was refluxed for 1 hour. The mixture was concentrated to dryness in vacuo and the residue was coevaporated with dry benzene. The residue was triturated with ether twice to give a white solid used directly in the next step.

Employing the procedure substantially as described in Example 4, Step A, but substituting for the 12-hydroxy-13-methyl-5,6,7,12-tetrahydrodibenzo[a,d]cycloocten-6,12-imine, an equimolecular amount of the 12-hydroxy-5,6,7,12-tetrahydrodibenzo[a,d]cycloocten-6,12-imines described in Table I there are produced the 12-chloro analogs also described in Table V, in accordance with the following reaction:

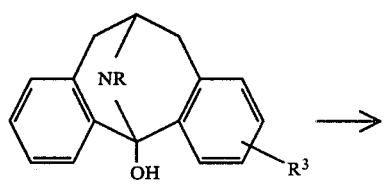

TABLE V

| R | R³ | R | R³ |
|---|---|---|---|
| H | H | H | 3-Br |
| —C₃H₇ | 2-Br | —CH₃ | 2-Br |
| —CH₂CH=CH₂ | H | —CH₂—⌬ | 2-Br |
| —CH₂—⌬ | H | —CH₃ | 2-Cl |
| —◁ | H | —CH₂—⌬ | 2-Cl |
| —⬡ | 2-Br | —CH₃ | 2-F |
| —CH₂—◁ | H | —CH₂—⌬ | 2-F |
| —CH₂CH₂—⌬ | H | | |

Step B: Preparation of 13-methyl-5,6,7,12-tetrahydrodibenzo[a,d]cycloocten-6,12-imine oxalate The product from Step A was suspended in a mixture of 10 ml. of dry ether and 20 ml of dry tetrahydrofuran and treated portionwise with 0.8 g. of a mineral oil suspension of lithium aluminum hydride (51.6% by weight) with stirring under nitrogen. The ultimate mixture was refluxed one hour and then stirred overnight at 20°–25° C. The mixture was treated with 1.5 ml. of water and the supernatant was decanted. The residue was extracted well with ether and the combined extracts were dried and concentrated to dryness. The oily residue was partitioned between benzene and 1 N aqueous HCl and the benzene was thoroughly extracted with additional 1 N HCl solution. The combined acid extract was basified with 10 N sodium hydroxide solution and extracted well with benzene. The benzene was washed with water, dried and concentrated to dryness. The residue (0.63 g.) was dissolved in 7 ml. of acetone and 7 drops of ethanol and treated with a solution of 0.27 g. of oxalic acid in 1 ml. of acetone. The product, 0.72 g., m.p. 176°–178° C. was collected and recrystallized twice from methanol to give 13-methyl-5,6,7,12-tetrahydrodibenzo[a,d]cycloocten-6,12-imine oxalate, m.p. 178°–180° C.

Employing the procedure substantially as described in Example 4, Step B, but substituting for the 12-chloro-13-methyl-5,6,7,12-tetrahydrodibenzo[a,d]cycloocten-6,12-imine used therein an equimolecular amount of the 12-bromo compounds described in Table II or the 12-chloro compounds described in Table V, there are produced the 5,6,7,12-tetrahydrodibenzo[a,d]cycloocten-6,12-imines unsubstituted in the 12-position described in Table VI in accordance with the following equation:

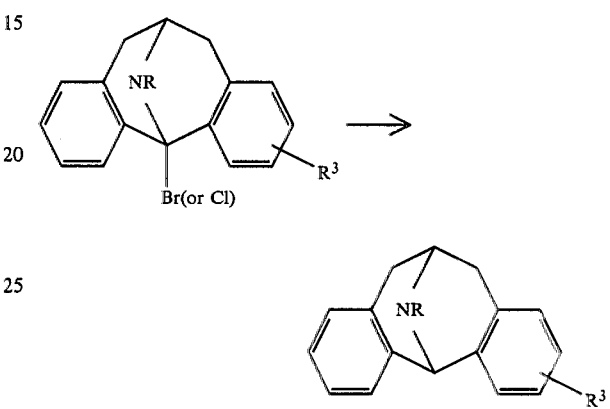

TABLE VI

| R | R³ | R | R³ |
|---|---|---|---|
| H | H | H | 3-Br |
| —C₃H₇ | 2-Br | —CH₃ | 2-Br |
| —CH₂CH=CH₂ | H | —CH₂—⌬ | 2-Br |
| —CH₂—⌬ | H | —CH₃ | 2-Cl |
| —◁ | H | —CH₂—⌬ | 2-Cl |
| —⬡ | 2-Br | —CH₃ | 2-F |
| —CH₂—◁ | H | —CH₂—⌬ | 2-F |
| —CH₂CH₂—⌬ | H | | |

EXAMPLE 5

12,13-Dimethyl-5,6,7,12-tetrahydrodibenzo[a,d]cycloocten-6,12-imine hydrochloride Step A: Preparation of 6,6-spiro(ethylenedioxy)-12-oxo-5,6,7,12-tetrahydrodibenzo[a,d]cyclooctene A mixture of 40 g. of 6,12-dioxo-5,6,7,12-tetrahydrodibenzo[a,d]cyclooctene, 35 ml. of ethylene glycol, 250 mg. of p-toluenesulfonic acid and 600 ml. of benzene was heated under reflux in a Dean-Stark apparatus for 22 hours. The cooled mixture was filtered and the solid was washed with water leaving solid A. The organic filtrate was dried (Na$_2$SO$_4$), filtered and concentrated to dryness. The residue was washed with a little cold benzene and with hexane leaving residue B. A and B were combined to give 44.3 g. of 6,6-spiro(ethylenedioxy)-12-oxo-5,6,7,12-tetrahydrodibenzo[a,d]cyclooctene, m.p. 195°–198° C.

Step B: Preparation of 12-methylene-5,6,7,12-tetrahydrodibenzo[a,d]cycloocten-6-one A solution (125 ml.) of 2.0 molar methyl lithium in ether was added dropwise with stirring to a slurry of 44.3 g. of the ethylenedioxy compound from Step A in 1 liter of ether. After stirring overnight, the mixture was poured into ice-water. The ether was separated and washed with 2×200 ml. of water, dried (Na$_2$SO$_4$), filtered and evaporated to dryness. The residue was treated with 400 ml. of chloroform and 200 ml. of 4 N aqueous hydrochloric acid and heated under reflux for 18 hours. The organic phase was washed with 2×150 ml. of water and the water was back-extracted with 150 ml. of chloroform. The combined chloroform layers were dried (MgSO$_4$), filtered and concentrated to dryness. The crystalline residue was washed with hexane to give 34.5 g. (94% from diketone) 12-methylene-5,6,7,12-tetrahydrodibenzo[a,d]cycloocten-6-one, m.p. 68°–70° C.

Step C: Preparation of 6-methylamino-12-methylene-5,6,7,12-tetrahydrodibenzo[a,d]cyclooctene and its hydrochloride salt The product from Step B (2.0 g.) was added to a solution of 6.5 g. of methylamine in 200 ml. of tetrahydrofuran. Some molecular seives were added as a drying agent and the mixture was stirred 1 hour. After cooling to 5° C., 3 g. of acetic acid was added, then after 15 minutes 3 g. of sodium cyanoborohydride was added and the mixture was stirred over the week-end (about 72 hours). The mixture was filtered and the filtrate was evaporated to dryness. The residue was treated with 150 ml. of water and concentrated hydrochloric acid to pH 1-2. After 1 hour the mixture was washed with 100 ml. ether and the ether was discarded. The mixture was made basic with aqueous ammonia and extracted with 3×100 ml. of ether. The combined extracts were dried (Na$_2$SO$_4$), filtered and concentrated to dryness. The residue was washed with hexane to give 1.9 g. of the free base of the product. This was dissolved in 20 ml. of 4 N methanolic hydrogen chloride and concentrated to dryness. The residue was triturated with ether and recrystallized from acetonitrile to give 1.9 g. 6-methylamino-12-methylene-5,6,7,12-tetrahydrodibenzo[a,d]cyclooctene hydrochloride, m.p. 238°–242° C. (dec.).

Step D: Preparation of 12,13-dimethyl-5,6,7,12-tetrahydrodibenzo[a,d]cycloocten-6,12-imine hydrochloride A mixture of 7.1 g. of the secondary amine from Step C, 4.6 g. of solid potassium hydroxide and 150 ml. of ethylene glycol was heated under reflux in a nitrogen atmosphere for 18 hours. Ethylene glycol (100 ml.) was distilled from the mixture at 62° C./0.3 mm Hg. and the reaction mixture was poured into 600 ml. of water and extracted with 3×250 ml. of ether. The extracts were combined, washed with 200 ml. of water, dried (Na$_2$SO$_4$), filtered and evaporated to dryness. The residue was slurried with 350 ml. of water containing 15 ml. of concentrated hydrochloric acid, washed with 100 ml. of ether, made basic with concentrated aqueous ammonia, and extracted with 3×150 ml. of ether. The ether extracts were combined, dried (Na$_2$SO$_4$), filtered and evaporated to dryness to give 5.8 g. of crude product. The crude material was dissolved in 75 ml. acetone and treated with 2.0 g. of oxalic acid in 25 ml. of hot acetone. Cooling deposited 6.0 g. of oxalate salt which was recrystallized from methanol to give 5.2 g. of oxalate salt. This was dissolved in 200 ml. of aqueous ammonia, and 250 ml. ether. The ether was separated, washed with water, dried (Na$_2$SO$_4$), filtered and evaporated to dryness. The residue was dissolved in 50 ml. of methanol and treated with 3.5 ml. of 11 N ethanolic hydrogen chloride. The mixture was concentrated to dryness. The residue was slurried with 200 ml. of ether and the solids (4.6 g.) were collected on a filter. This solid was refluxed with 100 ml. acetone, cooled in the freezer, filtered to give 3.7 g. of product with m.p. 249°–254° C. Recrystallization from 350 ml. of acetone after concentration to 150 ml. gave 3.1 g. of 12,13-dimethyl-5,6,7,12-tetrahydrodibenzo[a,d]cycloocten-6,12-imine hydrochloride, m.p. 252°–254° C.

Step D (Alternate): Preparation of 12,13-dimethyl-5,6,7,12-tetrahydrodibenzo[a,d]cycloocten-6,12-imine hydrogen oxalate To 2.1 g. (7.3 mmol) of 6-methylamino-12-methylene-5,6,7,12-tetrahydrodibenzo[a,d]cyclooctene hydrochloride stirred at room temperature under nitrogen in dry THF (75 ml.) was added butyllithium in hexane (6.5 ml., 1.6 M). The mixture was stirred for 2 hours, treated with ice water (2 ml.), and concentrated under reduced pressure. The residue was treated with water (50 ml.) and extracted with ether (3×25 ml.). The combined ether solutions were washed with water, dried over K$_2$CO$_3$, filtered, and evaporated to dryness under reduced pressure to give 12,13-dimethyl-5,6,7,12-tetrahydrodibenzo[a,d]cycloocten-6,12-imine as a yellow oil.

The oil, dissolved in acetone (2 ml.) was treated with oxalic acid (0.96 g., 0.01 mol) in acetone and refrigerated to give 12,13-dimethyl-5,6,7,12-tetrahydrodibenzo[a,d]cycloocten-6,12-imine hydrogen oxalate. (2.4 g., 96%) as a white powder. Recrystallization from methanol gave 1.2 g. (48%), m.p. 181.5°–3.5° C. (dec.).

EXAMPLE 6

12-Ethyl-13-methyl-5,6,7,12-tetrahydrodibenzo[a,d]cycloocten-6,12-imine hydrochloride

Step A: Preparation of 6,6-spiro(ethylenedixoy)-12-ethylidene-5,6,7,12-tetrahydrodibenzo[a,d]cyclooctene To a stirred slurry of ethyl triphenylphosphonium bromide (40.9 g., 0.11 mole) in ether (400 ml.) was added n-butyllithium in hexane (50.3 ml., 2.17 M). To the resulting solution was added a solution of 6,6-spiro(ethylenedioxy)-12-oxo-5,6,7,12-tetrahydrodibenzo[a,d]cyclooctene (29 g., 0.10 mole) in dry THF (300 ml.). After heating under reflux for 10 hours, the solvent was evaporated and the residue was distributed between H$_2$O (300 ml.) and HCCl$_3$ (500 ml.). The HCCl$_3$ solution was dried over Na$_2$SO$_4$, filtered and evaporated. The residue was chromatographed on silica-gel which was eluted with HCCl$_3$ to obtain 20.3 g. of 6,6,- spiro(ethylenedioxy)-12-ethylidene-5,6,7,12-tetrahydrodibenzo[a,d]cyclooctene, m.p. 84°–86° C.

Step B: Preparation of 12-ethylidene-5,6,7,12-tetrahydrodibenzo[a,d]cycloocten-6-one A solution of 6,6-spiro(ethylenedioxy)-12-ethylidene-5,6,7,12-tetrahydrodibenzo[a,d]cyclooctene (15.4 g., 0.053 mole) in HCCl$_3$ (400 ml.) was slurried and heated under reflux with 4 N aqueous HCl (200 ml.) for 3 hours. The HCCl$_3$ solution was separated, washed with H$_2$O and dried over Na$_2$SO$_4$. The drying agent was separated by filtration and the filtrate evaporated. The residue was recrystallized from acetonitrile to yield 11.8 g. of 12-ethylidene-5,6,7,12-tetrahydrodibenzo[a,d]cycloocten-6-one, m.p. 145°–147° C.

Employing the procedure substantially as described in Example 5, Steps C and D, but substituting for the 12-methylene-5,6,7,12-tetrahydrodibenzo[a,d]cycloocten-6-one used in Step C, there is produced in sequence:

Step C: 12-Ethylidene-6-methylamino-5,6,7,12-tetrahydrodibenzo[a,d]cyclooctene its hydrochloride salt; and Step D: 12-Ethyl-13-methyl-5,6,7,12-tetrahydrodibenzo[a,d]cycloocten-6,12-imine hydrochloride, or hydrogen oxalate Employing the procedure of Example 5 or 6, but substituting for the 6,12-dioxo-5,6,7,12-tetrahydrodibenzo[a,d]cyclooctene used in Step A of Example 5 an equimolecular amount of an R$^3$-substituted diketone described in Table VII and substituting for the methyl lithium used in Step B of Example 5, or the ethyl triphenylphosphonium bromide used in Step A of Example 6 an equimolecular amount of a compound of formula LiR$_{60}$$^2$ or (C$_6$H$_5$)$_3$P$^+$-R$_{60}$$^2$Br$^-$ respectively described in Table VII, and substituting for the methylamine used in Step C of Example 5 or 6, an equimolecular amount of an amine of formula R-NH$_2$ described in Table VII, there are produced the 5,6,7,12-tetrahydrodibenzo[a,d]cycloocten-6,12-imines also described in Table VII in accordance with the following reaction scheme:

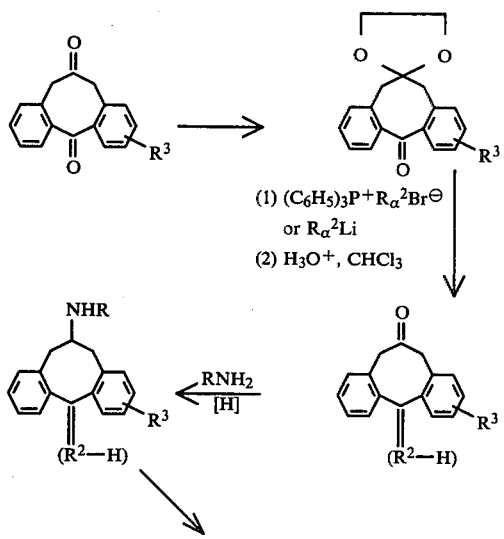

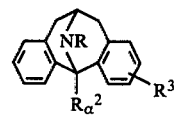

TABLE VII

| R | $R_a^2$ | $R^3$ | Procedure of Example |
|---|---|---|---|
| —C$_2$H$_5$ | —CH$_3$ | H | 5 |
| C$_2$H$_5$ | —CH$_3$ | 3-Br | 5 |
| —CH$_3$ | —CH$_3$ | 2-Br | 5 |
| —CH$_2$—◁ | —CH$_3$ | 2-Br | 5 |
| —CH$_2$—◁ | —CH$_3$ | H | 5 |
| —CH$_2$CH=CH$_2$ | —CH$_3$ | H | 5 |
| —CH$_3$ | —CH$_3$ | 2-Cl | 5 |
| —CH$_3$ | —CH$_3$ | 2-F | 5 |
| C$_2$H$_5$ | —CH$_3$ | 2-F | 5 |
| —CH$_3$ | —C$_2$H$_5$ | 2-Br | 6 |
| —CH$_3$ | —C$_3$H$_7$ | —H | 6 |
| —CH$_3$ | —C$_3$H$_7$ | 2-Br | 6 |
| —CH$_2$CH=CH$_2$ | —C$_2$H$_5$ | H | 6 |
| —CH$_2$CH=CH$_2$ | —CH$_3$ | 2-Br | 6 |

EXAMPLE 7

12-Methyl-5,6,7,12-tetrahydrodibenzo[a,d]cycloocten-6,12-imine

Step A: Preparation of 6-hydroximino-12-methylene-5,6,7,12-tetrahydrodibenzo[a,d]cyclooctene A mixture of 5.8 g. of 12-methylene-6-oxo-5,6,7,12-tetrahydrodibenzo[a,d]cyclooctene, 2.4 g. of hydroxylamine hydrochloride, 4.8 g. of sodium acetate trihydrate and 130 ml. of wet ether was stirred at room temperature for 24 hours. The supernatant was decanted from a solid and the residue was washed well with ether. The combined ether solutions were washed with 3×75 ml. of water, dried (Na$_2$SO$_4$) and concentrated to dryness to give 6.2 g. of white crystalline 6-hydroximino-12-methylene-5,6,7,12-tetrahydrodibenzo[a,d]cyclooctene, m.p. 119°–123° C.

Step B: Preparation of 6-hydroxylamino-12-methylene-5,6,7,12-tetrahydrodibenzo[a,d]cyclooctene A solution of 6.2 g. of oxime from Step A, 4.5 ml. of 7 N ethanolic hydrogen chloride and 200 ml. of methanol was stirred at room temperature and 2.1 g. of sodium cyanoborohydride was added in portions over 20 minutes. After 30 minutes another 2 ml. of 7 N ethanolic hydrogen chloride was added and stirring was continued another 1.5 hours. The solvent was evaporated and the residue was partitioned between chloroform and 5% (w/v) aqueous sodium hydroxide. The chloroform extract was washed with water, dried (MgSO$_4$) and concentrated to give 6.3 g. of a colorless glass of 6-hydroxylamino-12-methylene-5,6,7,12-tetrahydrodibenzo[a,d]cyclooctene.

Step C: Preparation of 13-hydroxy-5,6,7,12-tetrahydrodibenzo[a,d]cycloocten-6,12-imine A solution of 5 g. of the hydroxylamino compound from Step B in 200 ml. of dry xylene was added dropwise over 80 minutes to 200 ml. of refluxing dry xylene with stirring. After an additional 1.5 hour of refluxing, the solvent was evaporated in vacuo and the residue was crystallized from 50 ml. of 95% ethanol to give 2.6 g. of 13-hydroxy-5,6,7,12-tetrahydrodibenzo[a,d]cycloocten-6,12-imine, m.p. 186°–192° C.

Step D: Preparation of 12-methyl-5,6,7,12-tetrahydrodibenzo[a,d]cycloocten-6,12-imine Zinc dust (20.0 g.) was added in portions over 25 minutes to a stirred solution of 17.95 g. of the imine from Step C in 70 ml. of glacial acetic acid. After the exothermic reaction mixture cooled to about 60° 1 C., it was stirred for 2.5 hours at 60°–65° C. The mixture was cooled to room temperature, filtered and the precipitate was washed with acetic acid. The filtrate and washings were concentrated to dryness in vacuo. The residue was partitioned between ether and 10% (w/v) aqueous sodium hydroxide. The combined ether layers were washed with water, dried ($Na_2SO_4$) and concentrated to dryness to give 16.4 g. of 12-methyl-5,6,7,12-tetrahydrodibenzo[a,d]cycloocten-6,12-imine, m.p. 102°–104° C.

Employing the procedure substantially as described in Example 7 but substituting for the 12-methylene-6-oxo-5,6,7,12-tetrahydrodibenzo[a,d]cyclooctene used therein the 12-($R_{60}^2$-H)-6-oxo-compounds described in Table VIII, there are produced the 6,12-imines also described in Table VIII in accordance with the following reaction scheme:

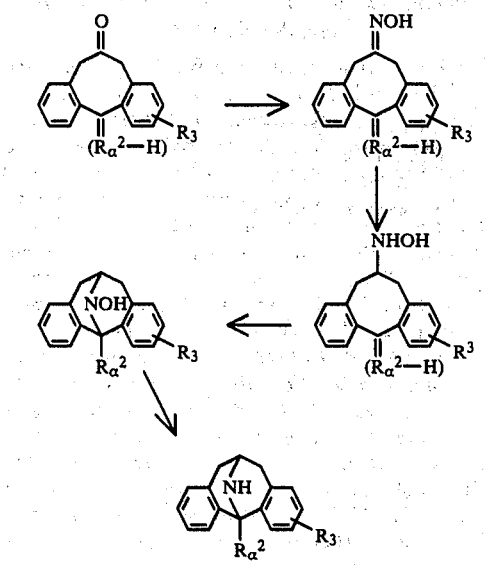

TABLE VIII

| $R_\alpha^2$ | $R^3$ |
|---|---|
| —$CH_3$ | 2-Br |
| —$CH_3$ | 2-Cl (m.p. 191–193° C., hydrogen maleate) |
| —$CH_3$ | 2-F |
| —$C_2H_5$ | H (m.p. 119–121° C.) |
| —$C_2H_5$ | 3-Br |
| —$C_3H_7$ | H |
| —$C_3H_7$ | 2-Br |

EXAMPLE 8

13-Benzyl-12-methyl-5,6,7,12-tetrahydrodibenzo[a,d]cycloocten-6,12-imine, hydrochloride A mixture of 2.6 g. of 12-methyl-5,6,7,12-tetrahydrodibenzo[a,d]cycloocten-6,12-imine, 1.55 g. of benzyl chloride, 3.2 g. of anhydrous sodium carbonate and 50 ml. of dioxane was stirred at reflux temperature for 5 days. The mixture was filtered and the filtrate was evaporated to dryness in vacuo to 4 g. of an oil. The oil was dissolved in 15 ml. of absolute ethanol, treated with 1.6 ml. of 7 N ethanolic hydrogen chloride and diluted with 70 ml. of absolute ether to precipitate 3.55 g. of product with m.p. 265°–270° C. This material was recrystallized from 25 ml. absolute ethanol to give 2.2 g. of product, m.p. 242°–262° C, which on combination with 300 mg. of similar material and recrystallization from a mixture of 8 ml. of methanol and 20 ml. of ether gave 2.15 g. of 13-benzyl-12-methyl-5,6,7,12-tetrahydrodibenzo[a,d]cycloocten-6,12-imine hydrochloride, m.p. 245° C. (dec.).

Employing the procedure substantially as described in Example 8, but substituting for the 12-methyl-5,6,7,12-tetrahydrodibenzo[a,d]cycloocten-6,12-imine and the benzyl chloride used therein equimolecular amounts, respectively, of a 12-$R_\alpha^2$-5,6,7,12-tetrahydrodibenzo[a,d]cycloocten-6,12-imine and a reagent of formula R-Br, described in Table IX there are produced the 12-$R_\alpha^2$-13-R-analogs also described in Table IX in accordance with the following reaction:

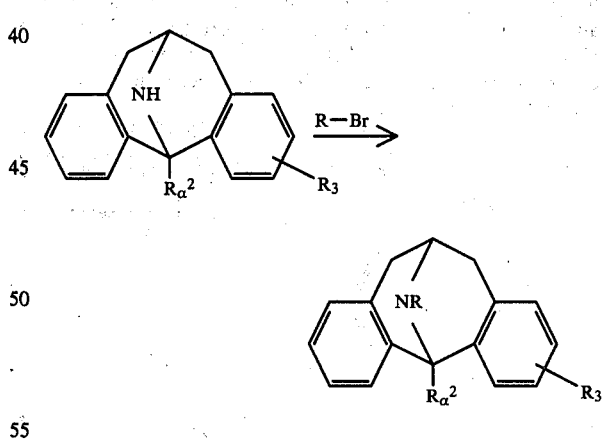

TABLE IX

| R | $R_\alpha^2$ | $R^3$ | R | $R_\alpha^2$ | $R^3$ |
|---|---|---|---|---|---|
| —$CH_2$—⌬ | —$CH_3$ | 2-Br | —$C_3H_7$ | —$CH_3$ | H |
| —$C_2H_5$ | —$CH_3$ | H | —$CH_2CH=CH_2$ | —$CH_3$ | H |
| —$C_2H_5$ | —$CH_3$ | 2-Br | —$CH_2$—◁ | —$CH_3$ | 2-Br |
| —$C_2H_5$ | —$C_2H_5$ | H | —$C_2H_5$ | —$CH_3$ | 2-Cl |
| —$C_2H_5$ | —$C_2H_5$ | 3-Br | —$C_2H_5$ | —$CH_3$ | 2-F |

EXAMPLE 9

6,12,13-Trimethyl-5,6,7,12-tetrahydrodibenzo[a,d]cyclooceten-6,12-imine

Step A: Preparation of 6-hydroxy-6-methyl-12-methylene-5,6,7,12-tetrahydrodibenzo[a,d]cyclooctene Magnesium turnings (3.03 g., 0.125 mole) were covered with 18 ml. of ether. A solution of 7.8 ml. (17.9 g., 0.126 mole) of methyl iodide in 37 ml. of ether was prepared, and about 3.5 ml. added to the magnesium slurry. The mixture was warmed gently to initiate Grignard reaction, and the remainder of the iodide solution was added at a rate sufficient to maintain a steady reflux. The mixture was held under a nitrogen blanket throughout.

Upon completion of the addition, the mixture was heated at reflux for one hour, then cooled to room temperature. A solution of 15.1 g. (0.065 mole) of 12-methylene-6-oxo-5,6,7,12-tetrahydrodibenzo[a,d]cyclooctene in 100 ml. of ether was added over 5 minutes to the stirred Grignard solution, and the resulting mixture was stirred for one hour at room temperature and quenched in 1 liter of ice water containing 5 g. of ammonium chloride. The resulting suspension was extracted three times with ether (200 ml.), and the combined ether layers were washed once with dilute aqueous sodium bisulfite, once with dilute sodium bicarbonate, and twice with water. The washed ether solution was dried over potassium carbonate, filtered, and evaporated *in vacuo* to give 6-hydroxy-6-methyl-12-methylene-5,6,7,12-tetrahydrodibenzo[a,d]cyclooctene as a colorless oil, 17.7 g.

Employing the procedure substantially as described in Example 9, Step A, but substituting for the methyl iodide and/or the 12-methylene-6-oxo-5,6,7,12-tetrahydrodibenzo[a,d]cyclooctene used therein equimolecular amounts, respectively, of a compound of formula $R^1$-I and/or the 6-oxo-5,6,7,12-tetrahydrodibenzo[a,d]cyclooctenes described in Table X, there are produced the carbinols also described in Table X in accordance with the following reaction:

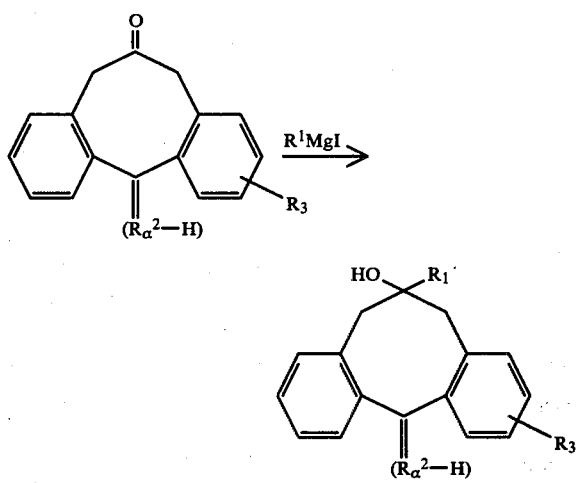

TABLE X

| $R^1$ | $R_\alpha^2$ | $R^3$ |
|---|---|---|
| —CH$_3$ | —CH$_3$ | 2-Br |
| —C$_2$H$_5$ | —CH$_3$ | H |

TABLE X-continued

| $R^1$ | $R_\alpha^2$ | $R^3$ |
|---|---|---|
| —C$_2$H$_5$ | —CH$_3$ | 2-Br |
| —CH$_2$—⟨phenyl⟩ | —CH$_3$ | H |
| —CH$_2$CH=CH$_2$ | —CH$_3$ | H |
| —⟨cyclopropyl⟩ | —CH$_3$ | H |
| —⟨cyclohexyl⟩ | —CH$_3$ | 2-Br |
| —CH$_3$ | —CH$_3$ | 2-Cl |
| —CH$_3$ | —CH$_3$ | 2-F |
| —CH$_3$ | —C$_2$H$_5$ | H |
| —CH$_3$ | —C$_2$H$_5$ | 3-Br |
| —CH$_3$ | —C$_3$H$_7$ | H |
| —CH$_3$ | —C$_3$H$_7$ | 2-Br |

Step B: Preparation of 6,12-dimethyl-6-hydroxy-5,6,7,12-tetrahydrodibenzo[a,d]cyclooctene Crude methylene compound from Step A (17.7 g.) in 100 ml. of absolute ethanol was treated with 1 g. of decolorizing carbon and filtered. An additional 80 ml. of ethanol was added followed by 0.5 g. of 10% Pd/charcoal catalyst, and the mixture was hydrogenated at 50 p.s.i.g. Hydrogenation was continued until hydrogen uptake ceased abruptly after uptake of one mole equivalent. The mixture was filtered and evaporated *in vacuo* to give 15.8 g. of crude 6,12-dimethyl-6-hydroxy-5,6,7,12-tetrahydrodibenzo[a,d]cyclooctene, m.p. 100°–135° C., a mixture of two isomers.

Step C: Preparation of 6-acetylamino-6,12-dimethyl-5,6,7,12-tetrahydrodibenzo[a,d]cyclooctene Dimethyl carbinol from Step B (11.5 g., 0.046 mole) was dissolved in 120 ml. of acetonitrile and added dropwise to 50 ml. of 95% sulfuric acid stirred in ice. The addition rate was controlled to maintain the temperature of the mixture at 15° C. Upon completion of the addition, the mixture was stirred for three hours at room temperature, then quenched in 700 ml. of ice water. The resulting slurry was stirred for 15 minutes, then filtered. The filtrate was extracted twice with chloroform and the filtered solids taken up in the same solvent (about 400 ml. total volume). The combined chloroform fractions were washed twice with water, once with sodium bicarbonate solution, and once again with water, dried over potassium carbonate, filtered, and evaporated *in vacuo*. The resulting solid was dried overnight *in vacuo* at 40° C. to give 13.2 g. of 6-acetylamino-6,12-dimethyl-5,6,7,12-tetrahydrodibenzo[a,d]cyclooctene, m.p. 185°–224° C. (mixture of isomers). Recrystallization from ethanol gave material with m.p. 232°–233.5° C.

Step D: Preparation of 6-(N-acetyl-N-methylamino)-6,12-dimethyl-5,6,7,12-tetrahydrodibenzo[a,d]cyclooctene Diisopropylamine (7.6 g., 0.075 mole) in 75 ml. of tetrahydrofuran (THF), previously dried over molecular sieves, was stirred in an ice bath and maintained under a nitrogen blanket while methyllithium in ether (42 ml. of 1.8 M solution, 0.076 mole) was added dropwise. The mixture was stirred in the ice bath for ½ hour, then transferred via syringe to an addition funnel fitted to a separate reaction vessel.

The latter vessel was charged with 12.7 g. (0.043 mole) of amide compound from Step C and 50 mg. of triphenylmethane dissolved in 150 ml. of THF. The amide solution was stirred in ice under a nitrogen blanket, and the lithium diisopropylamide solution was added dropwise at a rate slow enough to maintain the reaction temperature below 10° C. Addition was continued until the orange color of the triphenylmethide anion persisted. The mixture was stirred 15 minutes and treated with 17 ml. of methyl iodide in 20 ml. of THF added at such a rate as to hold the internal temperature below 10° C. The mixture was stirred one hour in an ice bath and another hour at room temperature.

The solution was quenched in 1.5 liter of ice-water and extracted three times with chloroform. The combined chloroform fractions were washed twice with water, twice with 1 N HCl, twice with dilute sodium bisulfite solution, and twice with water, dried over potassium carbonate, filtered and evaporated in vacuo to give 11.2 g., (0.036 mole) of 6-(N-acetyl-N-methylamino)-6,12-dimethyl-5,6,7,12-tetrahydrodibenzo[a,d]cyclooctene, m.p. 118°–187° C. (mixture of isomers). Chromatography on silica gel, elution with CHCl₃ and recrystallization from acetone/hexane, gave material with m.p. 150°–151.5° C.

Step E: Preparation of 6-(N-acetyl-N-methylamino)-6-methyl-12-methylene-5,6,7,12-tetrahydrodibenzo[a,d]cyclooctene The N-methylamide compound from Step E (11.9 g. (0.039 mole), 11 g. (0.048 mole) of 2,3-dichloro-5,6-dicyano-1,4-benzoquinone (DDQ), and 1.1 liters of benzene were combined and heated at reflux under nitrogen for 40 hours. The mixture was cooled, washed three times with 1 N sodium hydroxide solution and twice with water, dried over potassium carbonate, filtered, and evaporated in vacuo to give 11.4 g. of 6-(N-acetyl-N-methylamino)-6-methyl-12-methylene-5,6,7,12-tetrahydrodibenzo[a,d]cyclooctene, as a brown oil.

Step F: Preparation of 66,12,13-trimethyl-5,6,7,12-tetrahydrodibenzo[a,d]cycloocten-6,12-imine The N-methylamide from Step E 8.6 g. (0.033 mole) in 86 ml. of ethylene glycol was treated with 2.9 g. (0.052 mole) of potassium hydroxide and the mixture was heated at reflux under nitrogen for 24 hours. The solution was cooled, quenched in one liter of ice water, and the resulting slurry was extracted three times with chloroform.

The chloroform extracts were combined, washed with water, dried over potassium carbonate, filtered, and evaporated in vacuo to give 6.5 g. of orange-brown oil. The oil was treated with ethanolic HCl (excess) and evaporated in vacuo. The residue was twice triturated with ether and re-evaporated to give 10.4 g. of a crude grey solid. Recrystallization from ethanol gave, 6,12,13-trimethyl-5,6,7,12-tetrahydrodibenzo[a,d]cycloocten-6,12-imine hydrochloride, m.p. 287°–288° C.

Following the procedure of Example 9, Steps B through F but substituting for the 6-hydroxy-6-methyl-12-methylene-5,6,7,12-tetrahydrodibenzo[a,d]cyclooctene used in Step B and for the methyl iodide used in Step D, equimolecular amounts, respectively, of the carbinols and the iodides of formula R-I described in Table XI, there are produced the cycloocten-6,12-imines also described in Table XI in accordance with the following reaction scheme:

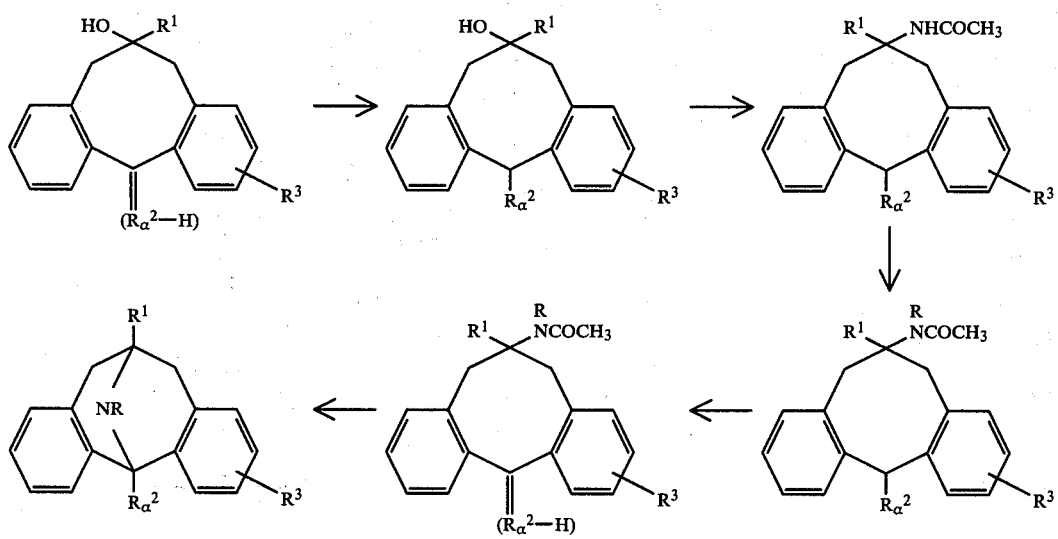

TABLE XI

| R | R¹ | Rₐ² | R³ |
|---|---|---|---|
| —CH₂—⌬ (phenyl) | —CH₃ | —CH₃ | H |
| —CH₃ | —CH₃ | —CH₃ | 2-Br |
| —CH₂CH=CH₂ | —C₂H₅ | —CH₃ | H |
| —CH₂—◁ (cyclopropyl) | —C₂H₅ | —CH₃ | 2-Br |
| —C₂H₅ | —CH₂—⌬ (phenyl) | —CH₃ | H |
| —C₂H₅ | —CH₂CH=CH₂ | —CH₃ | H |

TABLE XI-continued

| R | R¹ | $R_a^2$ | R³ |
|---|---|---|---|
| —CH₃ | —◁ | —CH₃ | H |
| —CH₃ | —⬡ | —CH₃ | 2-Br |
| —CH₃ | —CH₃ | —CH₃ | 2-Cl |
| —CH₃ | —CH₃ | —CH₃ | 2-F |
| —CH₃ | —CH₃ | —C₂H₅ | H |
| —C₂H₅ | —CH₃ | —C₂H₅ | 3-Br |
| —CH₃ | —CH₃ | —C₃H₇ | H |
| —CH₂—⬡(Ph) | —CH₃ | —C₃H₇ | 2-Br |

EXAMPLE 10

2-Methoxy-12,13-dimethyl-5,6,7,12-tetrahydrodibenzo[a,d]cycloocten-6,12-imine

A mixture of 0.00905 mol. of 2-bromo-12,13-dimethyl-5,6,7,12-tetrahydrodibenzo[a,d]cycloocten-6,12-imine, 0.81 mol. of sodium methoxide, 5.56 g. of electrolytic copper dust, and 87 ml. of DMF is stirred and heated on a steam bath for 2.5 hours. After cooling, 150 ml. of water and 150 ml. of ether is added to the mixture, and, after stirring, the mixture is filtered through a pad of celite. The ether phase is separated, washed with water, dried over magnesium sulfate, filtered, and the ether is removed on a rotary evaporator. The residue is dissolved in warm acetonitrile. On standing, the solution deposits crystals. The supernatant, containing the desired product, is decanted from the crystals. Evaporation of the solvent gives 2-methoxy-12,13-dimethyl-5,6,7,12-tetrahydrodibenzo[a,d]cycloocten-6,12-imine.

Employing the procedure substantially as described in Example 10, but substituting for the 2-bromo-12,13-dimethyl-5,6,7,12-tetrahydrodibenzo[a,d]cycloocten-6,12-imine and sodium methoxide used therein, equimolecular amounts, respectively, of the 2-bromo-compounds and sodium alkoxides described in Table XII, there are produced the 2-alkoxy-compounds also described in Table XII in accordance with the following reaction:

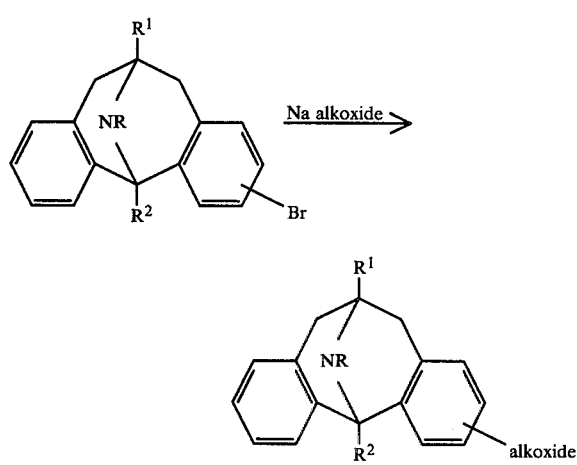

TABLE XII

| R | R¹ | R² | alkoxide |
|---|---|---|---|
| —C₃H₇ | H | —C₂H₅ | 2-OCH₃ |
| —⬡ | H | —C₂H₅ | 2-OC₂H₅ |
| —H | H | —CH₃ | 2-OCH₃ |
| —CH₃ | H | —C₂H₅ | 2-OC₂H₅ |
| —CH₂—⬡(Ph) | H | —CH₃ | 2-OCH₃ |
| —C₃H₇ | H | —OC₂H₅ | 2-OC₂H₅ |
| —⬡ | H | —OC₂H₅ | 2-OC₂H₅ |
| H —CH₃ | H H | —OCH₃ —OCH₃ | 2-OCH₃ 2-OCH₃ |
| —CH₂—⬡(Ph) | H | —OCH₃ | 2-OCH₃ |
| —C₃H₇ | H | H | 2-OCH₃ |
| —⬡ | H | H | 2-OC₃H₇ |
| —H —CH₃ | H H | H H | 2-OCH₃ 2-OCH₃ |
| —CH₂—⬡(Ph) | H | H | 2-OC₂H₅ |
| H | H | —C₂H₅ | 2-OCH₃ |
| —CH₂—◁ | H | —CH₃ | 2-OC₂H₅ |
| —C₂H₅ —CH₃ | —CH₃ —CH₃ | —C₂H₅ —CH₃ | 3-OCH₃ 2-OCH₃ |
| —CH₂—◁ | —C₂H₅ | —CH₃ | 2-OC₂H₅ |
| —CH₃ | —CH₂—⬡(Ph) | —C₂H₅ | 2-OCH₃ |
| —CH₃ | —⬡ | —CH₃ | 2-OCH₃ |

EXAMPLE 11

2-Cyano-6,12,13-trimethyl-5,6,7,12-tetrahydrodibenzo[a,d]cycloocten-6,12-imine

A mixture of 8.5 gm. (0.0249 mol) of 2-bromo-6,12,13-trimethyl-5,6,7,12-tetrahydrodibenzo[a,d]cycloocten-6,12-imine, 4.58 gm. (0.0498 mol) of cuprous cyanide, and 30 ml. of dry dimethylformamide is stirred and heated under reflux for 6.5 hr. To the cooled solution (25° C.) is added 54 ml. of water, 27 ml. of a saturated aqueous solution of sodium cyanide, and 75 ml. of benzene. The mixture is stirred until a two phase system is obtained. The benzene phase is removed and the aqueous phase is extracted with two 75 ml. portions of benzene. The combined benzene phases are washed with 100 ml. of aqueous 0.1 M sodium cyanide, three 100 ml. portions of water, and dried over magnesium sulfate.

After filtering, evaporation of the benzene gives a crystalline residue which is dissolved in the minimum volume of chloroform and passed over an alumina column (15"×1") packed in chloroform. The column is eluted with chloroform. Evaporation of the eluate provides 2-cyano-6,12,13-trimethyl-5,6,7,12-tetrahydrodibenzo[a,d cycloocten-6,12-imine.

Employing the procedure substantially as described in Example 11, but substituting for the 2-bromo-6,12,13-trimethyl-5,6,7,12-tetrahydrodibenzo[a,d]cycloocten-6,12-imine used therein, an equimolecular amount of the bromo-compounds described in Table XIII, there are produced the cyano-compounds also described in Table XIII in accordance with the following reaction:

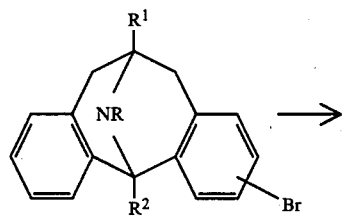

TABLE XIII

| R | R¹ | R² |
|---|---|---|
| —C₃H₇ | H | —C₂H₅ |
| —⌬ (cyclohexyl) | H | —C₂H₅ |
| —H | H | —CH₃ |
| —CH₃ | H | —C₂H₅ |
| —CH₂—⌬ (benzyl) | H | —CH₃ |
| —C₃H₇ | H | —OC₂H₅ |
| —⌬ (cyclohexyl) | H | —OC₂H₅ |
| H | H | —OCH₃ |
| —CH₃ | H | —OCH₃ |
| —CH₂—⌬ (benzyl) | H | —OCH₃ |
| —C₃H₇ | H | H |
| —⌬ (cyclohexyl) | H | H |
| —H | H | H |
| —CH₃ | H | H |
| —CH₂—⌬ (benzyl) | H | H |

TABLE XIII-continued

| R | R¹ | R² |
|---|---|---|
| H | H | —C₂H₅ |
| —CH₂—◁ | H | —CH₃ |
| —CH₃ | —CH₃ | —CH₃ |
| —CH₂—◁ | —C₂H₅ | —CH₃ |
| —CH₃ | —CH₂—⌬ (benzyl) | —C₂H₅ |
| —CH₃ | —⌬ (cyclohexyl) | —CH₃ |

EXAMPLE 12

2-Carboxy-6,12,13-trimethyl-5,6,7,12-tetrahydrodibenzo[a,d]cycloocten-6,12-imine A mixture of 0.92 gm. (0.00318 mol) of 2-cyano-6,12,13-trimethyl-5,6,7,12-tetrahydrodibenzo[a,d]cycloocten-6,12-imine and 20 ml. of 6 N hydrochloric acid is stirred and refluxed for 18 hours. After cooling, the mixture is filtered, and the collected solid is washed with 6 N hydrochloric acid and then with ethanol and dried to give 2-carboxy-6,12,13-trimethyl-5,6,7,12-tetrahydrodibenzo[a,d]cycloocten-6,12-imine.

Employing the procedure substantially as described in Example 12, but substituting for the 2-cyano-6,12,13-trimethyl-5,6,7,12-tetrahydrodibenzo[a,d]cycloocten-6,12-imine used therein, an equimolecular amount of the cyano-compounds described in Table XIV, there are produced the carboxy-compounds also described in Table XIV in accordance with the following reaction:

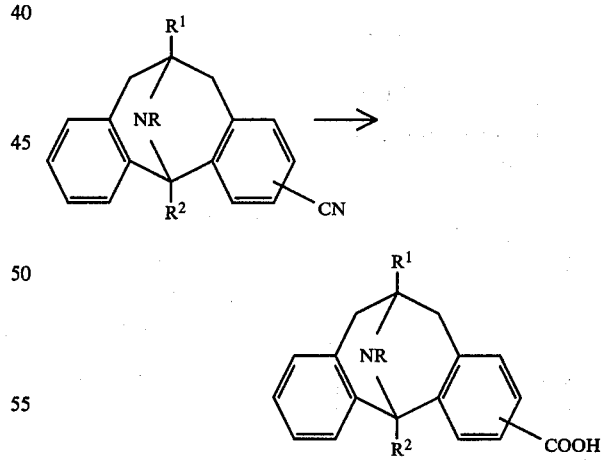

TABLE XIV

| R | R¹ | R² |
|---|---|---|
| —C₃H₇ | H | —C₂H₅ |
| —⌬ (cyclohexyl) | H | —C₂H₅ |
| —H | H | —CH₃ |
| —CH₃ | H | —C₂H₅ |

TABLE XIV-continued

| R | R¹ | R² |
|---|---|---|
| —CH₂—⌬ | H | —CH₃ |
| —C₃H₇ | H | —OC₂H₅ |
| —⌬(cyclohexyl) | H | —OC₂H₅ |
| H | H | —OCH₃ |
| —CH₃ | H | —OCH₃ |
| —CH₂—⌬ | H | —OCH₃ |
| —C₃H₇ | H | H |
| —⌬(cyclohexyl) | H | H |
| —H | H | H |
| —CH₃ | H | H |
| —CH₂—⌬ | H | H |
| H | H | —C₂H₅ |
| CH₂—▷ | H | —CH₃ |
| —CH₃ | —CH₃ | —CH₃ |
| —CH₂—▷ | —C₂H₅ | —CH₃ |
| —CH₃ | —CH₂—⌬ | —C₂H₅ |
| —CH₃ | —⌬(cyclohexyl) | CH₃ |

EXAMPLE 13

2-Trifluoromethylthio-6,12,13-trimethyl-5,6,7,12-tetrahydrodibenzo[a,d]cycloocten-6,12-imine A mixture of 2.24 g. (0.0353 mol) of copper dust, 3.90 g. (0.0097 mol) of bis-(trifluoromethylthio)-mercury, 1.65 g. (0.00484 mol) of 2-bromo-6,12,13-trimethyl-5,6,7,12-tetrahydrodibenzo[a,d]cycloocten-6,12-imine and 20 ml. of dimethylformamide is stirred and heated under reflux for six hours. The mixture is cooled in an ice bath and 100 ml. of chloroform and 30 ml. of concentrated ammonium hydroxide is added. The mixture is stirred overnight at room temperature and is filtered through a pad of diatomaceous earth. The filtrate and chloroform washings are combined and separated from the aqueous phase. The chloroform phase is washed with water, dried over magnesium sulfate, filtered, and the chloroform is removed on a rotary evaporator to give 2-trifluoromethylthio-6,12,13-trimethyl-5,6,7,12-tetrahydrodibenzo[a,d]cycloocten-6,12-imine.

Employing the procedure substantially as described in Example 13, but substituting for the 2-bromo-6,12,13-trimethyl-5,6,7,12-tetrahydrodibenzo[a,d]cycloocten-6,12-imine used therein, equimolecular amounts of the bromo- compounds described in Table XV, there are produced the trifluoromethylthio- compounds also described in Table XV in accordance with the following reaction:

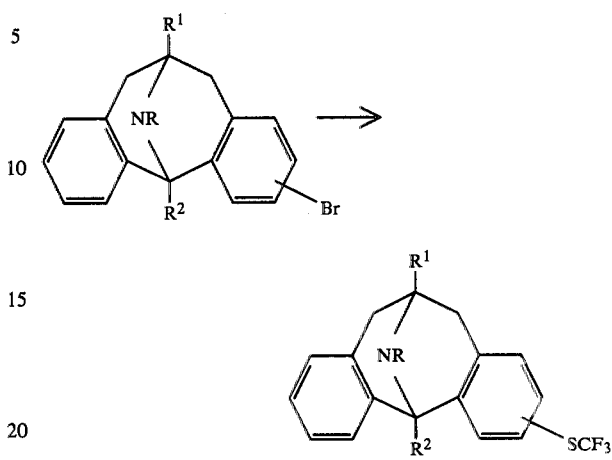

TABLE XV

| R | R¹ | R² |
|---|---|---|
| —C₃H₇ | H | —C₂H₅ |
| —⌬(cyclohexyl) | H | —C₂H₅ |
| —H | H | —CH₃ |
| —CH₃ | H | —C₂H₅ |
| —CH₂—⌬ | H | —CH₃ |
| —C₃H₇ | H | —OC₂H₅ |
| —⌬(cyclohexyl) | H | —OC₂H₅ |
| H | H | —OCH₃ |
| —CH₃ | H | —OCH₃ |
| —CH₂—⌬ | H | —OCH₃ |
| —C₃H₇ | H | H |
| —⌬(cyclohexyl) | H | H |
| —H | H | H |
| —CH₃ | H | H |
| —CH₂—⌬ | H | H |
| H | H | —C₂H₅ |
| —CH₂—▷ | H | —CH₃ |
| —CH₃ | —CH₃ | —CH₃ |
| —CH₂—▷ | —C₂H₅ | —CH₃ |
| —CH₃ | —CH₂—⌬ | —C₂H₅ |

TABLE XV-continued

| R | R¹ | R² |
|---|---|---|
| —CH₃ | —⬡ | —CH₃ |

EXAMPLE 14

3-Hydroxy-12,13-diethyl-6-methyl-5,6,7,12-tetrahydrodibenzo[a,d]cycloocten-6,12-imine A mixture of 3-methoxy-12,13-diethyl-6-methyl-5,6,7,12-tetrahydrodibenzo[a,d]cycloocten-6,12-imine (2.5 g.) and freshly fused pyridine hydrochloride (25 g.) is heated at 210°πC. for 20 minutes. The cooled mixture is slurried with water and the pH adjusted to 8.5 with concentrated ammonium hydroxide. The aqueous mixture is extracted with chloroform. The chloroform extract is washed with water, dried over $Na_2SO_4$, filtered and evaporated. Chromatography of the concentrate on silica gel eluted with chloroform gives 3-hydroxy-12,13-diethyl-6-methyl-5,6,7,12-tetrahydrodibenzo[a,d]cycloocten-6,12-imine.

Employing the procedure substantially as described in Example 14 but substituting for the 3-methoxy compound used there equimolecular amounts of the compounds described in Table XVI, there are produced the corresponding hydroxy compounds also described in Table XVI in accordance with the following reaction:

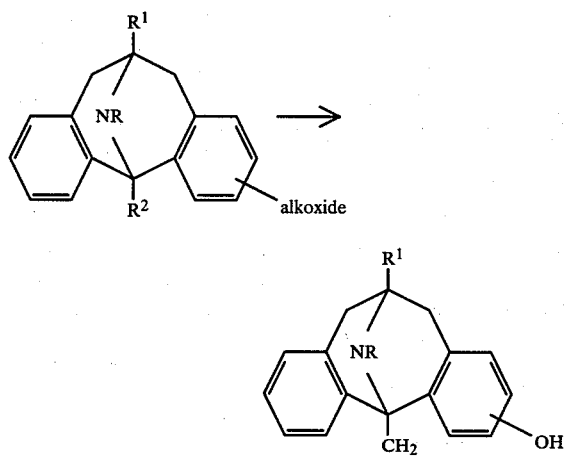

TABLE XVI

| R | R¹ | R² | —OH |
|---|---|---|---|
| —C₃H₇ | H | H | 2 |
| —⬡ | H | H | 2 |
| —H | H | H | 2 |
| —CH₃ | H | H | 2 |
| —CH₂—⬡ | H | H | 2 |
| H | H | —C₂H₅ | 2 |
| —CH₂—◁ | H | —CH₃ | 2 |
| —CH₃ | —CH₃ | —CH₃ | 2 |

TABLE XVI-continued

| R | R¹ | R² | —OH |
|---|---|---|---|
| —CH₂—◁ | —C₂H₅ | —CH₃ | 2 |
| —CH₃ | —CH₂—⬡ | —C₂H₅ | 2 |
| —CH₃ | —⬡ | —CH₃ | 2 |

EXAMPLE 15

13-Ethyl-12-methyl-5,6,7,12-tetrahydrodibenzo[a,d]cycloocten-6,12-imine

Step A: Preparation of 13-acetyl-12-methyl-5,6,7,12-tetrahydrodibenzo[a,d]cycloocten-6,12-imine Acetyl chloride (1.45 g.) was added dropwise to a stirred and ice-cooled solution of 3.5 g. of 12-methyl-5,6,7,12-tetrahydrodibenzo[a,d]cycloocten-6,12-imine and 2.0 g. of triethylamine in 60 ml. of absolute ether. After 20 hours at room temperature, the mixture was diluted with ether and filtered. The filtrate was evaporated and the residual solid recrystallized from ethanol-water to give 2.25 g. of white crystalline solid, m.p. 143°–144° C. The precipitate was suspended in water and extracted with ether. Evaporation of the washed and dried ether extract in vacuo gave 1.6 g. of white crystalline solid, m.p. 142°–144° C. The two crops were combined with 0.35 g. of similar material and recrystallized from 50% ethanol to give 4.1 g. of 13-acetyl-12-methyl-5,6,7,12-tetrahydrodibenzo[a,d]cycloocten-6,12-imine, m.p. 143°–144° C.

Step B: Preparation of 13-ethyl-12-methyl-5,6,7,12-tetrahydrodibenzo[a,d]cycloocten-6,12-imine A solution (10 ml.) of 0.98 molar diborane in tetrahydrofuran was added dropwise to a solution of 2.8 g. of the amide from Step A in 30 ml. of dry tetrahydrofuran with stirring and under nitrogen. After stirring overnight, the mixture was treated with water and the bulk of the tetrahydrofuran was distilled in vacuo. The residue was partitioned between ether and dilute sodium hydroxide. The ether layer was separated, washed with water, and extracted with 1 N hydrochloric acid. The acid extract was made basic with 5% (w/v) aqueous sodium hydroxide and extracted with ether-benzene (1:1). The washed and dried organic extract was evaporated in vacuo to give 1.75 g. of product, m.p. 152°–158° C. Two recrystallizations from 95% ethanol gave 1.35 g. of white crystalline 13-ethyl-12-methyl-5,6,7,12-tetrahydrodibenzo[a,d]-cycloocten-6,12-imine, m.p. 159°–161° C.

EXAMPLE 16

13-Benzyl-12-methyl-5,6,7,12-tetrahydrodibenzo[a,d]cycloocten-6,12-imine

To a solution of 12-methyl-5,6,7,12-tetrahydrodibenzo[a,d]cycloocten-6,12-imine (2.35 g.) and benzaldehyde (1.1 g.) in THF (100 ml.) is added acetic acid (1 ml.) and $NaCNBH_3$ (1.0 g.). The mixture is stirred for two days, filtered and the filtrate evaporated. The residue is slurried with 1 N aqueous $NH_4OH$ and extracted with HCCl₃. The HCCl₃ extract is dried over Na₂SO₄, filtered and evaporated. The residue is recrystallized from ethanol to yield 13-benzyl-12-methyl-5,6,7,12-tetrahydrodibenzo[a,d]cycloocten-6,12-imine.

EXAMPLE 17

13-Allyl-12-methyl-5,6,7,12-tetrahydrodibenzo[a,d]cycloocten-6,12-imine

A mixture of 2.6 g. of 12-methyl-5,6,7,12-tetrahydrodibenzo[a,d]cycloocten-6,12-imine, 1.8 g. of allyl bromide, 3 g. of anhydrous sodium carbonate and 50 ml. of dry benzene was stirred at reflux temperature for 20 hours. The mixture was filtered and the filtrate was evaporated to dryness in vacuo to give 1.6 g. of a solid, m.p. 90°–107° C. This product was combined with 0.275 g. of similar material and recrystallized twice from 95% ethanol to give 1.6 g. of white crystalline 13-allyl-12-methyl-5,6,7,12-tetrahydrodibenzo[a,d]cycloocten-6,12-imine, m.p. 112°–114° C.

EXAMPLE 18

13-Methyl-5,6,7,12-tetrahydrodibenzo[a,d]cycloocten-5,12-imine hydrogen chloride Step A: Preparation of cis and trans 2,3;5,6-dibenzo-8,8-dichloro-4-(N-methylamino)bicyclo[5.1.0] octane hydrogen chloride Methylamine was bubbled into 150 ml. of benzene stirred at room temperature until 3.1 g. (0.1 mole) had been absorbed. 2,3;5,6-Dibenzo-8,8-dichlorobicyclo[5.1.0]octan-4-one (7.5 g.; 0.026 mole) was added to the stirred solution followed by 0.013 mole (2.47 g., 1.43 ml.) of titanium tetrachloride dissolved in 20 ml. of benzene. The red slurry was stirred overnight. The mixture was concentrated in vacuo and treated with 75 ml. of acetonitrile followed by 2.3 g. (0.036 mole) of sodium cyanoborohydride. The slurry was stirred overnight at room temperature.

The mixture was treated with 100 ml. of 1 N NaOH and 150 ml. of water, and extracted three times with ether (100 ml.). The ether extracts were washed three times with water, dried over sodium sulfate, filtered, and evaporated in vacuo to give 8.9 g. of pale orange oil. The oil was dissolved in 50 ml. of methanol, treated with excess ethanolic HCl, and allowed to stand. The resulting white crystalline solid was separated by filtration and recrystallized from a mixture of 250 ml. of methanol and 150 ml. of ethanol to give trans 2,3;5,6-dibenzo-8,8-dichloro-4-(N-methylamino) bicyclo[5.1.-0]octane hydrogen chloride as a white crystalline solid, m.p. 280°–285° C. (d).

The mother liquor was concentrated in vacuo to 150 ml. and set aside to give cis 2,3;5,6-dibenzo-8,8-dichloro-4-(N-methylamino)bicyclo[5.1.0]octane hydrogen chloride as a white crystalline solid, m.p. 340° C.

Step B: Preparation of 6-chloro-13-methyl-5,12-dihydrodibenzo[a,d]cycloocten-5,12-imine hydrogen chloride 2,3;5,6-Dibenzo-8,8-dichloro-4-(N-methylamino)-bicyclo[5.1.0]octane hydrogen chloride (mixed isomers, predominantly trans) was stirred with ether and excess aqueous potassium hydroxide until homogeneous. The layers were separated and the aqueous layer was extracted twice with ether. The combined ether layers were washed with water, dried over sodium sulfate, filtered, and evaporated in vacuo to give 2,3;5,6-dibenzo-8,8-dichloro-4-(N-methylamino)bicyclo[5.1.0]octane (mixed isomers).

20 g. (0.066 mole) of this amine and 100 ml. of tetramethylurea were combined and heated at 200° under a reflux condenser and drying tube for 2 hours. The mixture was cooled, treated with 400 ml. of water and 65 ml. of 1 N sodium hydroxide, and extracted three times with ether. The combined ether fractions were washed with water, dried over sodium sulfate, filtered, and evaporated in vacuo to give 19.4 g. of crude brown solid. The solid was dissolved in 300 ml. of warm methanol, treated with 35 ml. of 8.3 N ethanolic HCl, and cooled for 2 hours to give unreacted cis-2,3;5,6-dibenzo-8,8-dichloro-4-(N-methylamino)-bicyclo[5.1.0]octane hydrogen chloride as a pale tan crystalline solid (5.56 g., 0.016 mole, 25%).

The mother liquor was concentrated in vacuo to a oil, treated with 600 ml. of acetone, and allowed to stand 2 hours at room temperature. White solid (1.4 g.) was filtered and the filtrate evaporated to a brown solid which was treated with 250 ml. of acetone, cooled, and scratched to give 6-chloro-13-methyl-5,12-dihydrodibenzo[a,d]cycloocten-5,12-imine hydrogen chloride (10.8 g., 0.035 mole, 53%), m.p. 224°–229° C. (d).

Step C: Preparation of 13-methyl-5,6,7,12-tetrahydrodibenzo[a,d]cycloocten-5,12-imine hydrogen chloride 6-Chloro-13-methyl-5,12-dihydrodibenzo[a,d]cycloocten-5,12-imine hydrogen chloride, (9.0 g., 29.6 mmole), 10 g. (102 mmole) of potassium acetate, and 1.0 g. of 10% palladium on charcoal were combined in 200 ml. of 95% ethanol and shaken under 50 p.s.i.g. of hydrogen until hydrogen uptake ceased. The mixture was filtered and evaporated in vacuo. The residue was treated with excess 1 M NaOH and extracted three times with ether. The ether extract was washed with water, dried over sodium sulfate, filtered, and evaporated in vacuo to give 6.6 g. of colorless oil. The oil was dissolved in 100 ml. of acetone, treated with 3.5 ml. of 8.4 M ethanolic hydrogen chloride, and evaporated in vacuo. Acetone was twice added and removed in vacuo, and the residue was scratched under acetone to give a white solid. Recrystallization from acetonitrile provided 13-methyl-5,6,7,12-tetrahydrodibenzo[a,d]cycloocten-5,12-imine hydrogen chloride, m.p. 246.5°–248.5° C.

Employing the procedure substantially as described in Example 18, Steps A through C, but substituting for the 2,3;5,6-dibenzo-8,8-dichlorobicyclo[5.1.0]octane-4-one used in Step A, an equimolecular amount of the corresponding 2-bromo-, 2-chloro- and 2-fluoro- derivatives thereof and substituting for the methylamine used in Step A an equimolecular amount of an amine of formula RNH₂, there are produced, the $R^3$, $R^4$-13-R-5,6,7,12-tetrahydrodibenzo[a,d]cycloocten-5,12-imine and hydrogen chloride salts described in Table XVII in accordance with the following reaction scheme:

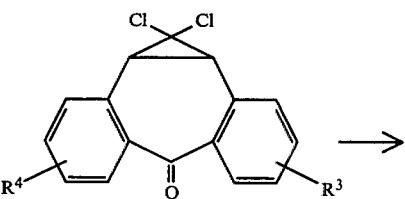

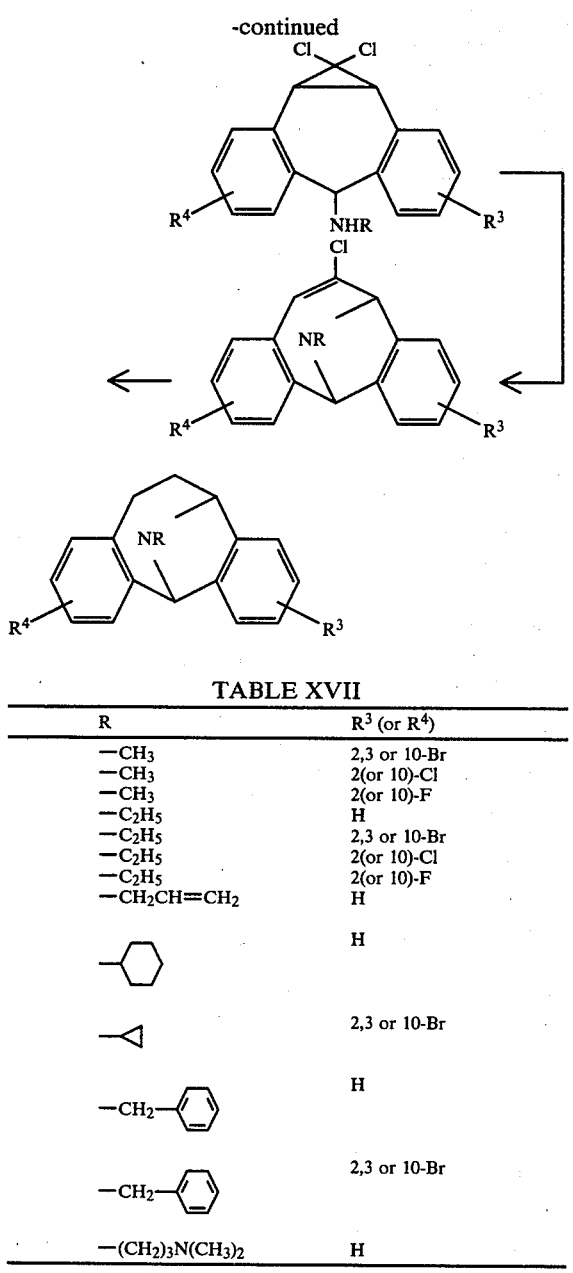

TABLE XVII

| R | R³ (or R⁴) |
|---|---|
| —CH₃ | 2,3 or 10-Br |
| —CH₃ | 2(or 10)-Cl |
| —CH₃ | 2(or 10)-F |
| —C₂H₅ | H |
| —C₂H₅ | 2,3 or 10-Br |
| —C₂H₅ | 2(or 10)-Cl |
| —C₂H₅ | 2(or 10)-F |
| —CH₂CH=CH₂ | H |
| —⟨cyclohexyl⟩ | H |
| —◁ (cyclopropyl) | 2,3 or 10-Br |
| —CH₂—⟨phenyl⟩ | H |
| —CH₂—⟨phenyl⟩ | 2,3 or 10-Br |
| —(CH₂)₃N(CH₃)₂ | H |

EXAMPLE 19

13-Methyl-5,6,7,12-tetrahydrodibenzo[a,d]cycloocten-5,12-imine hydrogen oxalate

Step A: Preparation of 13-methyl-5,12-imino-5,6,7,12-tetrahydrodibenzo[a,d]cycloocten-12-ol 5 g. (22.5 mmole) of 5,6,7,12-tetrahydrodibenzo[a,d]cycloocten-12-one, 3.8 g. (23.8 mmole) of bromine, and 10 mg. of dibenzoyl peroxide were combined in 100 ml. of carbon tetrachloride and heated at reflux for 24 hours with stimultaneous irradiation by a 275 watt General Electric ® sunlamp. The mixture was cooled, washed with dilute sodium bisulfite solution, then with water, dried over sodium sulfate, filtered, and evaporated in vacuo to give 8.5 g. of brown oil. The oil was combined with 8 g. (0.258 mole) of liquid methylamine condensed in a stainless steel bomb and heated at 50° C. for 1.5 hours. The bomb was cooled, carefully vented, and rinsed out with chloroform. The chloroform layer was washed twice with water, then extracted three times with 0.5 M citric acid. The combined acid fractions were washed with chloroform, made basic with 1 M NaOH, and extracted three times with ether. The ether fraction was washed with water, dried over sodium sulfate, filtered, and evaporated in vacuo to give 1.4 g. of pale tan solid. Recrystallization from 95% ethanol gave 0.6 g. of 13-methyl-5,12-imino-5,6,7,12-tetrahydrodibenzo[a,d]cycloocten-12-ol, m.p. 170°–171.8° C.

Step B: Preparation of 13-methyl-5,6,7,12-tetrahydrodibenzo[a,d]cycloocten-5,12-imine hydrogen oxalate 13-Methyl-5,12-imino-5,6,7,12-tetrahydrodibenzo[a,d]cycloocten-12-ol (1.2 g., 4.8 mmole) was heated in 15 ml. of refluxing thionyl chloride for 20 minutes. The mixture was cooled, evaporated in vacuo, treated with 30 ml. of toluene, and again evaporated in vacuo. The residue of 12-chloro-13-methyl-5,6,7,12-tetrahydrodibenzo[a,d]cycloocten-5,12-imine was washed with petroleum ether (decanted), and dried in a steam of nitrogen. The residue was dissolved in 20 ml. of tetrahydrofuran and added dropwise to a stirred slurry of 1 g. (0.026 mole) of lithium aluminum hydride in 20 ml. of tetrahydrofuran under nitrogen. The mixture was heated at reflux for 40 minutes, cooled, and hydrolyzed by careful dropwise addition of water. The resulting mass was filtered and the solids washed with dilute sodium hydroxide and ether.

The filtrate was diluted with 200 ml. of water, made basic with sodium hydroxide solution, and extracted three times with ether. The combined ether fractions were washed with water and extracted three times with 1 N hydrochloric acid. The combined acid fractions were made basic with sodium hydroxide solution and extracted twice with ether. The ether layers were combined, washed with water, dried over sodium sulfate, filtered and evaporated in vacuo.

The residue (800 mg.) was chromatographed on 65 g. of silica gel by elution with chloroform and 2%, 4%, 6%, and 10% methanol in chloroform. The product fraction was evaporated to give 450 mg. (1.92 mmole) of oil. The oil was dissolved in 3 ml. of acetone and treated with 1.92 mmole (173 mg.) of oxalic acid in 1 ml. of acetone. The solution was evaporated in vacuo and twice treated with ether and re-evaporated. The residue was crystallized from 30 ml. of acetone to give 270 mg. of pale tan solid, m.p. 186.5°–188° C.

EXAMPLE 20

12-Ethyl-13-methyl-5,6,7,12-tetrahydrodibenzo[a,d]cycloocten-5,12-imine hydrochloride Employing the procedure substantially as described in Example 2, but substituting for the 12-bromo-13-methyl-5,6,7,12-tetrahydrodibenzo[a,d]cycloocten-6,12-imine used therein, an equimolecular amount of 12-chloro-13-methyl-5,6,7,12-tetrahydrodibenzo[a,d]cycloocten-5,12-imine, there is produced 12-ethyl-13-methyl-5,6,7,12-tetrahydrodibenzo[a,d]cycloocten-5,12-imine hydrochloride.

EXAMPLE 21

12,13-Dimethyl-5,6,7,12-tetrahydrodibenzo[a,d]cycloocten-5,12-imine hydrogen chloride

Step A: Preparation of 12-methyl-5,6,7,12-tetrahydrodibenzo[a,d]cycloocten-6-one 31.4 g. (0.134 mole) of 12-methylene-5,6,7,12-tetrahydrodibenzo[a,d]cycloocten-6-one and 270 mg. of 10% palladium on charcoal were combined in 225 ml. of 95% ethanol and shaken under 50 p.s.i.g. of hydrogen. When hydrogen uptake ceased at about 1 mole equivalent, the mixture was filtered and evaporated *in vacuo* to give 31.1 g. of white solid, m.p. 152°–155° C.

Step B: Preparation of 12-methyl-5,6,7,12-tetrahydrodibenzo[a,d]cycloocten-6-ol 12-Methyl-5,6,7,12-tetrahydrodibenzo[a,d]cycloocten-6-one (3.6 g., 15.3 mmole) in 25 ml. of methanol was treated with several drops of 1 M sodium hydroxide followed by 0.58 g. (15.3 mmole) of sodium borohydride in 5 ml. of water. The mixture was heated at reflux for 20 minutes, cooled, and concentrated *in vacuo*. The residue was slurried in water and extracted three times with chloroform. The chloroform fractions were washed with water, dried over sodium sulfate, filtered, and evaporated *in vacuo* to give 3.7 g. of white solid, m.p. 142°–145° C.

Step C: Preparation of 12-methyl-7,12-dihydrodibenzo[a,d]cyclooctene

12-Methyl-5,6,7,12-tetrahydrodibenzo[a,d]cycloocten-6-ol (2.7 g., 0.011 mole) in 50 ml. of pyridine was treated with 15 ml. of phosphorous oxychloride. The mixture was heated at reflux for 45 minutes, cooled, and poured carefully into 600 ml. of stirred ice water. The resulting mixture was extracted three times with ether, and the combined ether layers were washed once with water, once with 1 N hydrochloric acid, and twice with water. The washed ether solution was dried over potassium carbonate, filtered, and evaporated *in vacuo* to give 1.9 g. of colorless oil.

Step D: Preparation of 5-(N-acetylamino)-12-methyl-5,6,7,12-tetrahydrodibenzo[a,d]cyclooctene 12-Methyl-7,12-dihydrodibenzo[a,d]cyclooctene (5 g., 22.7 mmole) in 70 ml. of acetonitrile was added dropwise to a stirred, cooled mixture of 2.5 ml. of water and 18 ml. of concentrated sulfuric acid at a rate that allowed the reaction temperature to be held below 30° C. Upon completion of the addition, the mixture was stirred overnight at room temperature. Thin layer chromatography (silica gel plate, chloroform elution) showed appreciable starting olefin still present.

Another 30 ml. of concentrated sulfuric acid was added and the mixture was stirred at room temperature another three hours. The solution was poured into 1 L of ice water and extracted 3 times with chloroform. The chloroform extracts were combined, washed twice with dilute sodium bicarbonate solution and twice with water, dried over potassium carbonate, filtered, and evaporated *in vacuo* to give 8.7 g. of orange oil which was triturated with petroleum ether to give 6.0 g. of pale tan solid. A sample crystallized from chloroform/hexane had m.p. 164.5°–166° C.

Step E: Preparation of 5-(N-acetyl-N-methylamino)-12-methyl-5,6,7,12-tetrahydrodibenzo[a,d]cyclooctene To 10 g. (99 mmole) of diisopropylamine in 100 ml. of dry tetrahydrofuran stirred in an ice bath under nitrogen was added 1.6 M methyllithium in ether (61 ml., 97.6 mmole). On completion of the addition, the solution was stirred for 15 minutes then transferred by syringe to an equilibrating addition funnel.

18.1 g. (64.9 mmole) of 5-(N-acetylamino)-12-methyl-5,6,7,12-tetrahydrodibenzo[a,d]cyclooctene in 200 ml. of dry tetrahydrofuran was treated with 0.3 g. of triphenylmethane and stirred in an ice bath under nitrogen. The amide solution was added dropwise from the addition funnel at a rate sufficiently slow to maintain the reaction temperature below 15° C., until the color of the triphenylmethide anion persisted. The mixture was stirred for 15 minutes in the ice bath, then treated with 20 ml. (45.6 g., 314 mmole) of methyliodide added rapidly (<5 min). The resulting solution was stirred for 2 hours, with the temperature held below 30° C. by ice cooling as necessary, then treated with 30 ml. of water. Nitrogen was bubbled through the mixture overnight, and the remaining liquid evaporated *in vacuo*. The residue was treated with 300 ml. of water and extracted three times with chloroform. The chloroform extracts were washed once with dilute sodium bisulfite solution and twice with water, dried over potassium carbonate, filtered, and evaporated *in vacuo* to 33 g. of red oil. The oil was washed four times with petroleum ether and evaporated *in vacuo* to give 16.0 g. of foam which was dissolved in 10 ml. of warm toluene, diluted with 250 ml. of diethyl ether, and refrigerated overnight to precipitate unreacted starting amide. The solution was filtered and the filtrate was evaporated *in vacuo* to give 5-(N-acetyl-N-methylamino)-12-methyl-5,6,7,12-tetrahydrodibenzo[a,d]cyclooctene, (10.5 g.) as an orange oil.

Step F: Preparation of 5-(N-acetyl-N-methylamino)-12-methylene-5,6,7,12-tetrahydrodibenzo[a,d]cyclooctene 5-(N-Acetyl-N-methylamino)-12-methyl-5,6,7,12-tetrahydrodibenzo[a,d]cyclooctene (10.5 g., 34 mmole), dichlorodicyanobenzoquinone (9.5 g. of 98%, 41 mmole) and 750 ml. of benzene were combined and heated at reflux under nitrogen for 3.5 hours. The mixture was cooled, washed four times with 1 M sodium hydroxide solution and twice with water, dried over potassium carbonate, treated with about 0.5 g. of decolorizing carbon, filtered, and evaporated *in vacuo* to give 10.5 g. of brown oil.

Step G: Preparation of 12,13-dimethyl-5,6,7,12-tetrahydrodibenzo[a,d]cycloocten-5,12-imine hydrogen chloride To 9.5 g. (32.6 mmole) of 5-(N-acetyl-N-methylamino)-12-methylene-5,6,7,12-tetrahydrodibenzo[a,d]cyclooctene in 166 ml. of ethylene glycol was added potassium hydroxide (7.6 g., 0.136 mole). The solution was heated at reflux under nitrogen for 22 hours, cooled, and quenched in 2 L of ice water. The resulting suspension was extracted three times with chloroform and the chloroform extracts were washed with water. The chloroform solution was extracted 4 times with 0.5 M citric acid. The combined citrate fractions were made basic with 1 M sodium hydroxide and extracted 3 times with chloroform. The chloroform extracts were washed twice with water, dried over potassium carbonate, filtered, and evaporated in vacuo to give 3.5 g. of yellow oil.

The oil was treated with 8 ml. of acetic anhydride, stirred at room temperature for 20 minutes, then diluted with 100 ml. of water. The mixture was made basic with 1 M NaOH, and extracted three times with chloroform. The combined extracts were washed with water, then extracted 3 times with 0.5 M citric acid. The combined acid fractions were washed with chloroform, made basic with 1 M sodium hydroxide, and extracted with chloroform 3 times. The combined extracts were washed once with water, dried over potassium carbonate, filtered, and evaporated *in vacuo* to give 2.6 g. of yellow oil.

The oil was dissolved in 95% ethanol and treated with excess ethanolic HCl. The solution was evaporated *in vacuo*, treated twice with ethanol, and re-evaporated. The residue was treated with ether, again evaporated, then crystallized from acetone to give a white solid, m.p. 243°–244.5° C.

Following the procedure substantially as described in Example 21, but substituting for the 12-methylene-5,6,7,12-tetrahydrodibenzo[a,d]cycloocten-6-one used in Step A, and for the methyl iodide used in Step E, equimolecular amounts, respectively of the substituted 12-$R_\alpha^2$-5,6,7,12-tetrahydrodibenzo[a,d]cycloocten-6-ones and iodides described in Table XVIII, there are produced the 5,6,7,12-tetrahydrodibenzo[a,d]cycloocten-5,12-imines also described in Table XVIII in accordance with the following reaction scheme.

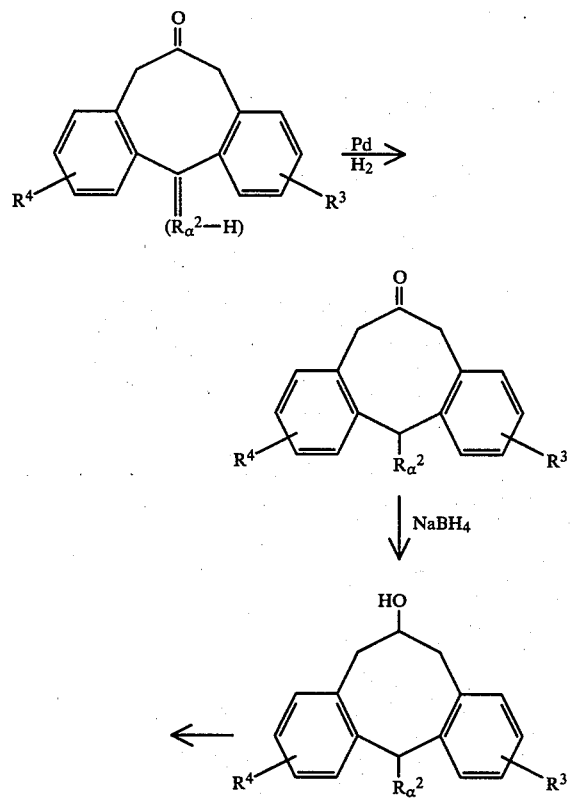

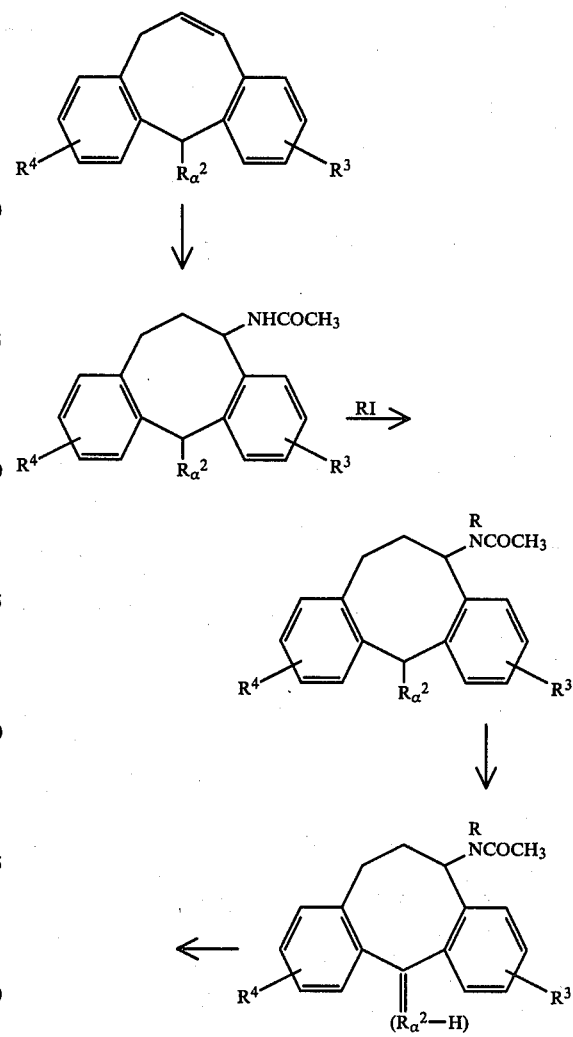

TABLE XVIII

| R | $R_\alpha^2$ | $R^3$(or $R^4$) |
|---|---|---|
| CH₂—⌬ | —CH₃ | H |
| —CH₃ | —CH₃ | 2,3 or 10-Br |
| —CH₂CH=CH₂ | —CH₃ | H |
| —CH₂—◁ | —CH₃ | 2,3 or 10-Br |
| —C₂H₅ | —CH₃ | H |
| —CH₃ | —CH₃ | 2(or 10)-Cl |
| —CH₃ | —CH₃ | 2(or 10)-F |
| —CH₃ | —C₂H₅ | H |
| —C₂H₅ | —C₂H₅ | 2,3 or 10-Br |
| —CH₃ | —C₃H₇ | H |

TABLE XVIII-continued

| R | $R_\alpha^2$ | $R^3$(or $R^4$) |
|---|---|---|
| 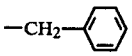 | —$C_3H_7$ | 2,3 or 10-Br |

EXAMPLE 22

2,3 or 10-Cyano-12,13-dimethyl-5,6,7,12-tetrahydrodibenzo[a,d]cycloocten-5,12-imine A mixture of 8.2 gm. (0.0249 mol) of 2,3 or 10-bromo-12,13-dimethyl-5,6,7,12-tetrahydrodibenzo[a,d]cycloocten-5,12-imine, 4.58 gm. (0.0498 mol) of cuprous cyanide, and 30 ml. of dry dimethylformamide is stirred and heated under reflux for 6.5 hr. To the cooled solution (25° C.) is added 54 ml. of water, 27 ml. of a saturated aqueous solution of sodium cyanide, and 75 ml. of benzene. The mixture is stirred until a two phase system is obtained. The benzene phase is removed and the aqueous phase is extracted with two 75 ml. portions of benzene. The combined benzene phases are washed with 100 ml. of aqueous 0.1 M sodium cyanide, three 100 ml. portions of water, and dried over magnesium sulfate. After filtering, evaporation of the benzene gives a crystalline residue which is dissolved in the minimum volume of chloroform and passed over an alumina column (15"×1") packed in chloroform. The column is eluted with chloroform. Evaporation of the eluate provides 2,3 or 10-cyano-12,13-dimethyl-5,6,7,12-tetrahydrodibenzo[a,d]cycloocten-5,12-imine.

Employing the procedure substantially as described in Example 22, but substituting for the 2,3 or 10-bromo-12,13-dimethyl-5,6,7,12-tetrahydrodibenzo[a,d]cycloocten-5,12-imine used therein, an equimolecular amount of the 2(or 10)-bromo compounds described in Table XIX there are produced the 2,3 or 10-cyano-compounds also described in Table XIX in accordance with the following reaction:

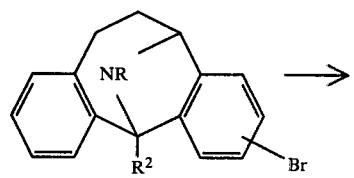 →

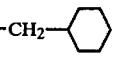

TABLE XIX

| R | $R^2$ |
|---|---|
| —$C_2H_5$ | H |
| 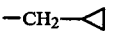 | H |
| —$CH_3$ | H |

TABLE XIX-continued

| R | $R^2$ |
|---|---|
| —$CH_2$—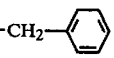 | H |
| —$CH_2$—◁ | —$CH_3$ |
| —$C_2H_5$ | —$C_2H_5$ |
| —$CH_2$— | —$C_3H_7$ |

EXAMPLE 23

2,3 or 10-Carboxy-12,13-dimethyl-5,6,7,12-tetrahydrodibenzo[a,d]cycloocten-5,12-imine A mixture of 0.87 gm. (0.00318 mol) of 2,3 or 10-cyano-12,13-dimethyl-5,6,7,12-tetrahydrodibenzo[a,d]cycloocten-5,12-imine and 20 ml. of 6 N hydrochloric acid is stirred and refluxed for 18 hours. After cooling, the mixture is filtered, and the collected solid is washed with 6 N hydrochloric acid and then with ethanol and dried to give 2,3 or 10-carboxy-12,13-dimethyl-5,6,7,12-tetrahydrodibenzo[a,d]cycloocten-5,12-imine.

Employing the procedure substantially as described in Example 23, but substituting for the 2,3 or 10-cyano-12,13-dimethyl-5,6,7,12-tetrahydrodibenzo[a,d]cycloocten-5,12-imine used therein, an equimolecular amount of the 2,3 or 10-cyano-compounds described in Table XX, there are produced the 2,3 or 10-carboxy-compounds also described in Table XX in accordance with the following reaction:

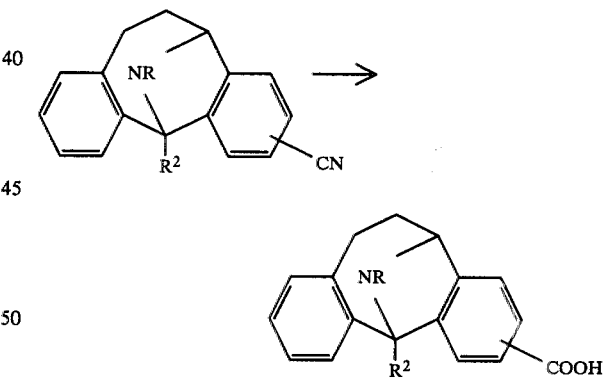

TABLE XX

| R | $R^2$ |
|---|---|
| —$C_2H_5$ | H |
| ◁ | H |
| —$CH_3$ | H |
| —$CH_2$—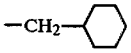 | H |
| —$CH_2$—◁ | —$CH_3$ |
| —$C_2H_5$ | —$C_2H_5$ |

TABLE XX-continued

| R | R² |
|---|---|
| 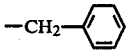 | —C₃H₇ |

EXAMPLE 24

2,3 or 10-Trifluoromethylthio-12,13-dimethyl-5,6,7,12-tetrahydrodibenzo[a,d]cycloocten-5,12-imine A mixture of 2.24 g. (0.0353 mol) of copper dust, 3.90 g. (0.0097 mol) of bis-(trifluoromethylthio)-mercury, 1.6 g. (0.00484 mol) of 2,3 or 10-bromo-12,13-dimethyl-5,6,7,12-tetrahydrodibenzo[a,d]cycloocten-5,12-imine and 20 ml. of dimethylformamide is stirred and heated under reflux for six hours. The mixture is cooled in an ice bath and 100 ml. of chloroform and 30 ml. of concentrated ammonium hydroxide is added. The mixture is stirred overnight at room temperature and is filtered through a pad of diatomaceous earth. The filtrate and chloroform washings are combined and separated from the aqueous phase. The chloroform phase is washed with water, dried over magnesium sulfate, filtered, and the chloroform is removed on a rotary evaporator to give 2,3 or 10-trifluoromethylthio-12,13-dimethyl-5,6,7,12-tetrahydrodibenzo[a,d]cycloocten-5,2-imine.

Employing the procedure substantially as described in Example 24, but substituting for the 2,3 or 10-bromo-12,13-dimethyl-5,6,7,12-tetrahydrodibenzo[a,d]cycloocten-5,12-imine used therein, equimolecular amounts of the bromo-compounds described in Table XXI, there are produced the trifluoromethylthio-compounds also described in Table XXI in accordance with the following reaction:

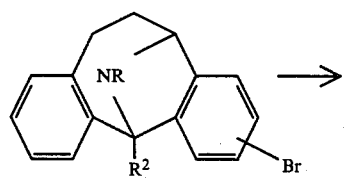

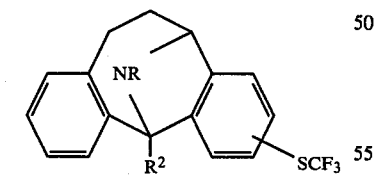

TABLE XXI

| R | R² |
|---|---|
| —C₂H₅ | H |
| —◁ | H |
| —CH₃ | H |
| —CH₂—⌬ | H |
| —CH₂—◁ | —CH₃ |
| —C₂H₅ | —C₂H₅ |

TABLE XXI-continued

| R | R² |
|---|---|
| 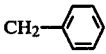 | —C₃H₇ |

EXAMPLE 25

13-Methyl-5,12-dihydrodibenzo[a,d]cycloocten-5,12-imine hydrogen chloride 58.6% Lithium aluminum hydride mineral oil suspension (1.28 g., 19.7 mmole) was washed twice with petroleum ether and the solvent was removed by decantation. The residue was treated with 30 ml. of tetrahydrofuran followed by 0.8 ml. (1.38 g., 7.3 mmole) of titanium tetrachloride in 20 ml. of tetrahydrofuran added dropwise with stirring. The resulting mixture was stirred for 15 minutes, then treated with 2.0 g. (6.6 mmole) of 6-chloro-13-methyl-5,12-dihydrodibenzo[a,d]cycloocten-5,12-imine hydrogen chloride (from Example 15, Step C), added as the solid in portions. The mixture was heated at reflux under nitrogen for four hours, cooled, and hydrolyzed by careful addition of 0.75 ml. of water, 0.75 ml. of 15% aqueous sodium hydroxide, and 2.25 ml. of water. The mixture was stirred for 15 minutes and filtered, and the solids were washed with warm chloroform. The filtrate was evaporated in vacuo and the residue was stirred with 50 ml. of 1 M sodium hydroxide for two hours. The mixture was extracted three times with chloroform, all chloroform fractions were combined, washed with water, dried over sodium sulfate, filtered, and evaporated in vacuo. The oil was treated with excess 9 N ethanolic hydrogen chloride and evaporated in vacuo. Acetone was twice added and removed in vacuo. The residue was recrystallized from acetone to give 13-methyl-5,12-dihydrodibenzo[a,d]cycloocten-5,12-imine hydrogen chloride, m.p. 244°-254° C. (dec.).

Employing the procedure substantially as described in Example 25, but substituting for the 6-chloro-13-methyl-5,12-dihydrodibenzo[a,d]cycloocten-5,12-imine hydrogen chloride, equimolecular amounts of the 6-chloro-13-R-5,12-dihydrodibenzo[a,d]cycloocten-5,12-imines described in Table XVI there are produced the 13-R-5,12-dihydrodibenzo[a,d]cycloocten-5,12-imines described in Table XXII respectively, in accordance with the following reaction scheme:

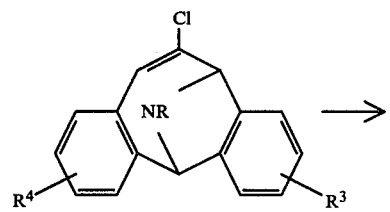

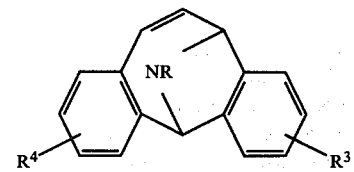

TABLE XXII

| R | R³(or R⁴) |
|---|---|
| —CH₃ | 2,3 or 10-Br |
| —CH₃ | 2(or 10)-Cl |
| —CH₃ | 2(or 10)-F |
| —C₂H₅ | H |
| —C₂H₅ | 2,3 or 10-Br |
| —C₂H₅ | 2(or 10)-Cl |
| —C₂H₅ | 2(or 10)-F |
| —CH₂CH=CH₂ | H |
| —⟨cyclohexyl⟩ | H |
| —⟨cyclopropyl⟩ | 2,3 or 10-Br |
| —CH₂—⟨phenyl⟩ | H |
| —CH₂—⟨phenyl⟩ | 2,3 or 10-Br |
| —(CH₂)₃N(CH₃)₂ | H |

Employing the procedures substantially as described in Examples 23 and 24, but substituting for the starting materials employed therein equimolecular amounts of the 2,3 or 10-cyano- and 2,3 or 10-trifluoromethylthio- compounds described in Table XXIII in accordance with the following reaction.

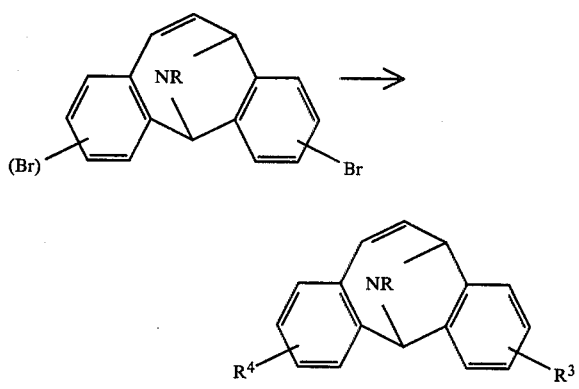

TABLE XXIII

| R | R³(or R⁴) |
|---|---|
| —CH₃ | 2,3 or 10-CN |
| —C₂H₅ | 2,3 or 10-CN |
| —⟨cyclopropyl⟩ | 2,3 or 10-CN |
| —CH₂—⟨phenyl⟩ | 2,3 or 10-CN |
| —CH₃ | 2,3 or 10-SCF₃ |
| —C₂H₅ | 2,3 or 10-SCF₃ |
| —⟨cyclopropyl⟩ | 2,3 or 10-SCF₃ |
| —CH₂—⟨phenyl⟩ | 2,3 or 10-SCF₃$_{hz,1/32}$ |

Similarly, employing the procedure of Example 23, but substituting for the starting material employed therein an equimolecular amount of the 2,3 or 10-cyano compounds of Table XXIII, there are produced the 2,3 or 10-carboxy compounds listed below in accordance with the following equation:

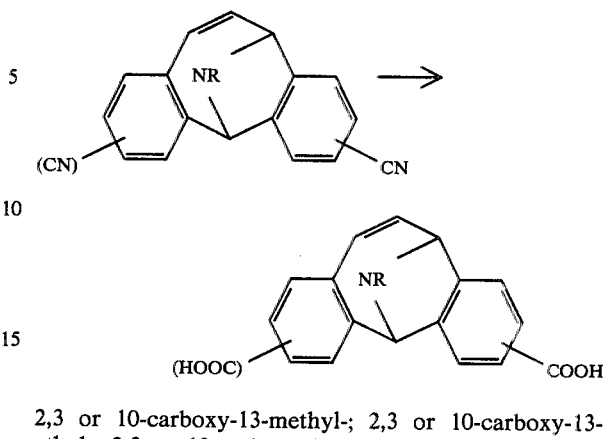

2,3 or 10-carboxy-13-methyl-; 2,3 or 10-carboxy-13-ethyl-; 2,3 or 10-carboxy-13-cyclopropyl-; and 2,3 or 10-carboxy-13-benzyl-5,12-dihydro-dibenzo[a,d]cyclocten-5,12-imine.

EXAMPLE 26

Preparation of Intravenous Solutions

A solution containing 10 mg. of 12,13-dimethyl-5,6,7,12-tetrahydrodibenzo[a,d]cycloocten-6,12-imine hydrochloride per ml. of injectable solution is prepared in the following manner.

A mixture of 10 mg. of 12,13-dimethyl-5,6,7,12-tetrahydrodibenzo[a,d]cycloocten-6,12-imine hydrochloride and 9 mg. of sodium chloride is dissolved in sufficient water for injection to make 1 ml. of solution. The pH is adjusted using hydrochloric acid or aqueous sodium hydroxide to about pH 7.0.

If it is desired that the intravenous solution be used for multi-dose purposes, 1.0 mg. of methyl-p-hydroxybenzoate (methyl paraben) and 0.10 mg. of n-propyl-p-hydroxy benzoate (propyl paraben) are mixed with the other solids before adding water to dissolve the solids. The solution is prepared and stored in such a manner that it is suitably protected from the deleterious effects of the atmosphere. One method by which this can be accomplished is by preparation and storage of the solution in an atmosphere of nitrogen. The resulting solution is sterilized by autoclaving. Injectable solutions comprising 0.1, 1.0, 100.0 mg., respectively, of 12,13-dimethyl-5,6,7,12-tetrahydrodibenzo[a,d]cycloocten-6,12-imine hydrochloride per ml. of solution are similarly prepared substituting the indicated amount for the above-illustrated 10 mg. of quantity. Bulk injectable solutions of convenient volume for subsequent delivery in unit dosage form are readily prepared following the above procedure.

Following the above procedure, other representative injectable solutions of the present invention are prepared when the 12,13-dimethyl-5,6,7,12-tetrahydrodibenzo[a,d]cycloocten-6,12-imine hydrochloride is replaced by an equivalent amount of any of the novel compounds of the present invention.

EXAMPLE 27

Tablet Preparation

Tablets containing 1.0, 2.0, 25.0, 26.0, 50.0, and 100.0 mg., respectively, of 12-methyl-5,6,7,12-tetrahydrodibenzo[a,d]cycloocten-6,12-imine hydrochloride are prepared as illustrated below.

| TABLE FOR DOSES CONTAINING FROM 1–25 MG. OF THE ACTIVE COMPOUND | | | |
|---|---|---|---|
| | Amount - mg. | | |
| 12-methyl-5,6,7,12-tetrahydrodibenzo-[a,d]cycloocten-6,12-imine hydrochloride | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26–100 MG. OF THE ACTIVE COMPOUND | | | |
|---|---|---|---|
| | Amount - mg. | | |
| 12-methyl-5,6,7,12-tetrahydrodibenzo[a,d]cycloocten-6,12-imine hydrochloride | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | .39 | 0.75 | 1.5 |

All of the active compound, lactose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg., 2.0 mg., 25.0 mg., 26.0 mg., 50.0 mg., and 100.0 mg. of active ingredient per tablet. Other tablets are prepared using the same procedures and the equivalent amounts of excipients along with equivalent amounts of any of the novel compounds of the present invention.

What is claimed is:

1. A method of treating anxiety, depression, muscle spasm, convulsions, mixed anxiety-depression, minimal brain dysfunction and extrapyramidal disorders comprising administering to a patient in need of such treatment an effective amount of a compound of structural formula:

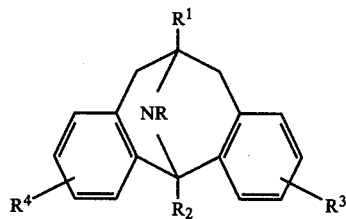

or a pharmaceutically acceptable salt thereof, wherein R is hydrogen or $C_{1-3}$alkyl; $R^2$ is $C_{1-3}$alkyl, and $R^1$, $R^3$ and $R^4$ are all hydrogen.

2. The method of claim 1 wherein the compound is 12-methyl-5,6,7,12-tetrahydrodibenzo[a,d]cycloocten-6,12-imine or a pharmaceutically acceptable salt thereof.

3. A pharmaceutical composition useful as an anxiolytic, antidepressant, anticonvulsant, muscle relaxant, or in the treatment of mixed anxiety-depression, minimal brain dysfunction or extrapyramidal disorders comprising a pharmaceutical carrier and an effective amount of a compound of structural formula:

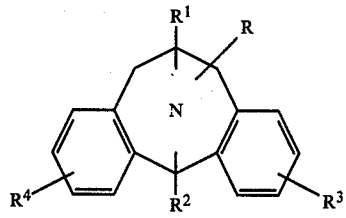

or a pharmaceutically acceptable salt thereof, wherein R is hydrogen or $C_{1-3}$alkyl; $R^2$ is $C_{1-3}$alkyl, and $R^1$, $R^3$ and $R^4$ are all hydrogen.

4. The composition of claim 3, wherein the compound is 12-methyl-5,6,7,12-tetrahydrodibenzo[a,d]cycloocten-6,12-imine or a pharmaceutically acceptable salt thereof.

* * * * *